United States Patent [19]
Goulet et al.

[11] Patent Number: 6,156,767
[45] Date of Patent: Dec. 5, 2000

[54] ANTAGONISTS OF GONADOTROPIN RELEASING HORMONE

[75] Inventors: Mark Goulet, Westfield; Matthew J. Wyvratt, Jr., Mountainside; Peter Lin, Edison; Lin Chu, Scotch Plains; Narindar N. Girotra, Old Bridge, all of N.J.

[73] Assignee: Merck & Co., Inc., Rahway, N.J.

[21] Appl. No.: 09/083,477

[22] Filed: May 22, 1998

Related U.S. Application Data

[60] Provisional application No. 60/048,638, Jun. 5, 1997, and provisional application No. 60/048,642, Jun. 5, 1997.

[51] Int. Cl.[7] .................. C07D 217/00; C07D 401/00; C07D 215/12; A61K 31/56

[52] U.S. Cl. .................. 514/307; 514/308; 514/314; 514/333; 514/339; 546/140; 546/148; 546/176; 546/256; 546/277.1

[58] Field of Search .................. 546/140, 148, 546/176, 256, 277.1; 514/307, 308, 314, 333, 339

[56] References Cited

U.S. PATENT DOCUMENTS

| | | | |
|---|---|---|---|
| 4,252,803 | 2/1981 | Webb | 514/415 |
| 4,544,663 | 10/1985 | Manning et al. | 514/378 |
| 4,943,572 | 7/1990 | von Angerer | 514/235.2 |
| 5,030,640 | 7/1991 | Fisher et al. | 514/339 |
| 5,756,507 | 5/1998 | Goulet et al. | 514/255 |
| 5,780,437 | 7/1998 | Goulet et al. | 514/79 |

FOREIGN PATENT DOCUMENTS

| | | |
|---|---|---|
| 879381 | 2/1980 | Belgium . |
| 0 219 292 A2 | 4/1987 | European Pat. Off. . |
| 0 679 642 A1 | 11/1995 | European Pat. Off. . |
| 2181559 | 12/1973 | France . |
| WO90/05721 | 5/1990 | WIPO . |
| WO95/29900 | 11/1995 | WIPO . |
| WO97/21703 | 6/1997 | WIPO . |
| WO97/21707 | 6/1997 | WIPO . |

OTHER PUBLICATIONS

J. Med. Chem, vol. 32, pp. 2036–2038 (1989), by Clark, et al.
Annu. Rev. Med. vol. 45, pp. 391–405 (1994), by P. M. Conn, et al.
Drugs of the Future, vol. 13, No. 8, pp. 761–787 (1988), by A. S. Dutta.
Current Opinion in Obstetrics & Gynecology, vol. 6, pp. 262–268 (1994), by R. A. Loy.
TEM, vol. 3, No., pp. 30–34 (1992), by L. R. Barbieri.
Drugs, vol. 35, pp. 63–82 (1988), by M. Filicor, et al.
Human Reproduction, vol. 11, Suppl. 3, pp. 89–101 (1996), by U. Cirkel.
Human Reproduction, vol. 11, Suppl. 1, pp. 123–132 (1996), by G. Hodgen.

*Primary Examiner*—D. Margaret Seaman
*Attorney, Agent, or Firm*—Elliott Korsen; Mark R. Daniel

[57] ABSTRACT

There are disclosed compounds of formula (I)

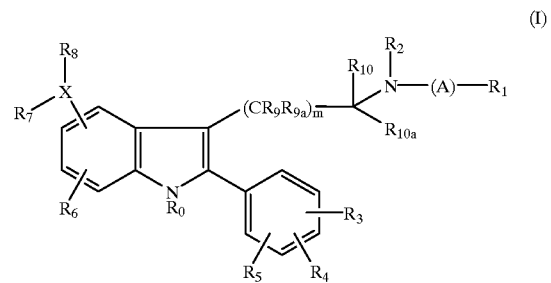

and pharmaceutically acceptable salts thereof which are useful as antagonists of GnRH and as such may be useful for the treatment of a variety of sex-hormone related and other conditions in both men and women.

28 Claims, No Drawings

ANTAGONISTS OF GONADOTROPIN RELEASING HORMONE

This application claims priority to Provisional Application Ser. No. 60/048,638, Jun. 5, 1997 and 60/048,642, filed Jun. 5, 1997.

BACKGROUND OF THE INVENTION

The gonadotropin-releasing hormone (GnRH), also referred to as luteinizing hormone-releasing hormone (LHRH), is a decapeptide that plays a key role in human reproduction. The hormone is released from the hypothalamus and acts on the pituitary gland to stimulate the biosynthesis and secretion of luteinizing hormone (LH) and follicle-stimulating hormone (FSH). LH released from the pituitary gland is primarily responsible for the regulation of gonadal steroid production in both sexes, whereas FSH regulates spermatogenesis in males and follicular development in females. GnRH agonists and antagonists have proven effective in the treatment of certain conditions which require inhibition of LH/FSH release. In particular, GnRH-based therapies have proven effective in the treatment of endometriosis, uterine fibroids, polycystic ovarian disease, precocious puberty and several gonadal steroid-dependent neoplasia, most notably cancers of the prostate, breast and ovary. GnRH agonists and antagonists have also been utilized in various assisted fertilization techniques and have been investigated as a potential contraceptive in both men and women. They have also shown possible utility in the treatment of pituitary gonadotrophe adenomas, sleep disorders such as sleep apnea, irritable bowel syndrome, premenstrual syndrome, benign prostatic hyperplasia, hirsutism, as an adjunct to growth hormone therapy in growth hormone deficient children, and in murine models of lupus.

Current GnRH antagonists are GnRH-like decapeptides which are generally administered intravenously or subcutaneously presumably because of negligible oral activity. These have amino acid substitutions usually at positions one, two, three, six and ten.

Non-peptide GnRH antagonists offer the possible advantage of oral administration. Non-peptide GnRH antagonists have been described in European Application 0 219 292 and in De, B. et al., J. Med. Chem., 32, 2036–2038 (1989), in WO 95/28405, WO 95/29900 and EP 0679642 all to Takeda Chemical Industries, Ltd.

Substituted indoles known in the art include those described in the following patents and patent applications. U.S. Pat. No. 5,030,640 discloses alpha-heterocyclic ethanol aminoalkyl indoles which are potent β-agonists. U.S. Pat. No. 4,544,663 discloses indolamine derivatives which are allegedly useful as male anti-fertility agents. WO 90/05721 discloses alpha-amino-indole-3-acetic acids useful as anti-diabetic, anti-obesity and anti-atherosclerotic agents. French patent 2,181,559 discloses indole derivatives with sedative, neuroleptic, analgesic, hypotensive, antiserotonin and adrenolytic activity. Belgian patent 879381 discloses 3-aminoalkyl-1H-indole-5-thioamide and carboxamide derivatives as cardiovascular agents used to treat hypertension, Raynaud's disease and migraine. WO 97/21435, WO 97/21703, WO 97/21707 and WO 97/21704 disclose non-peptidyl, indole derivatives as GnRH antagonists.

SUMMARY OF THE INVENTION

The present invention relates to compounds which are non-peptide antagonists of GnRH which can be used to treat a variety of sex-hormone related conditions in men and women, to methods for their preparation, and to methods and pharmaceutical compositions containing said compounds for use in mammals.

Because of their activity as antagonists of the hormone GnRH, the compounds of the present invention are useful to treat a variety of sex-hormone related conditions in both men and women. These conditions include endometriosis, uterine fibroids, polycystic ovarian disease, hirsutism, precocious puberty, gonadal steroid-dependent neoplasias such as cancers of the prostate, breast and ovary, gonadotrophe pituitary adenomas, sleep apnea, irritable bowel syndrome, premenstrual syndrome and benign prostatic hypertophy. They are also useful as an adjunct to treatment of growth hormone deficiency and short stature, and for the treatment of systemic lupus erythematosis. Further, the compounds of the invention may be useful in in vitro fertilization and as contraceptives. The compounds may also be useful in combination with androgens, estrogens, progesterones, antiestrogens and antiprogestogens for the treatment of endometriosis, fibroids and in contraception. They may also be useful in combination with testosterone or other androgens or antiprogestogens in men as a contraceptive. The compounds may also be used in combination with an angiotensin-converting enzyme inhibitor such as Enalapril or Captopril, an angiotensin II-receptor antagonist such as Losartan or a renin inhibitor for the treatment of uterine fibroids. Additionally, the compounds of the invention may also be used in combination with bisphosphonates (bisphosphonic acids) and other agents, such as growth hormone secretagogues, e.g. MK-0677, for the treatment and prevention of disturbances of calcium, phosphate and bone metabolism, in particular, for the prevention of bone loss during therapy with the GnRH antagonist, and in combination with estrogens, progesterones, antiestrogens, antiprogestins and/or androgens for the prevention or treatment of bone loss or hypogonadal symptoms such as hot flashes during therapy with the GnRH antagonist.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-20 androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoromethylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

Further, a compound of the present invention may be used in combination or co-administered with a compound having luteinizing hormone releasing activity such as a peptide or natural hormone or analog thereof Such peptide compounds include leuprorelin, gonadorelin, buserelin, triptorelin, goserelin, nafarelin, histrelin, deslorelin, meterlin and recirelin.

DETAILED DESCRIPTION OF THE INVENTION

The present invention relates to compounds of the general formula

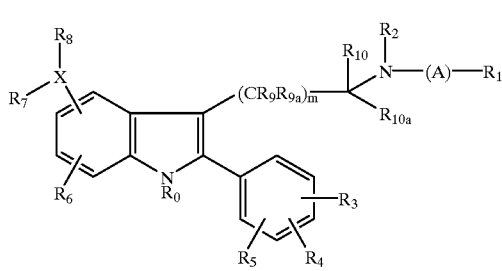

(I)

wherein

A is $C_1-C_6$ alkyl, substituted $C_1-C_6$ alkyl, $C_3-C_7$ cycloalkyl, substituted $C_3-C_7$ cycloalkyl, $C_3-C_6$ alkenyl, substituted $C_3-C_6$ alkenyl, $C_3-C_6$ alkynyl, substituted $C_3-C_6$ alkynyl, $C_1-C_6$ alkoxy, or $C_0-C_5$ alkyl-$S(O)_n-$$C_0-C_5$ alkyl, $C_0-C_5$ alkyl-O-$C_0-C_5$ alkyl, $C_0-C_5$ alkyl-$NR_{18}$-$C_0-C_5$ alkyl where $R_{18}$ and the $C_0-C_5$ alkyl can be joined to form a ring,

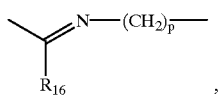

or a single bond;

$R_0$ is hydrogen, $C_1-C_6$ alkyl, substituted $C_1-C_6$ alkyl, wherein the substituents are as defined below; aryl, substituted aryl, aralkyl or substituted aralkyl, wherein the substituents are as defined for $R_3$, $R_4$ and $R_5$;

$R_1$ is

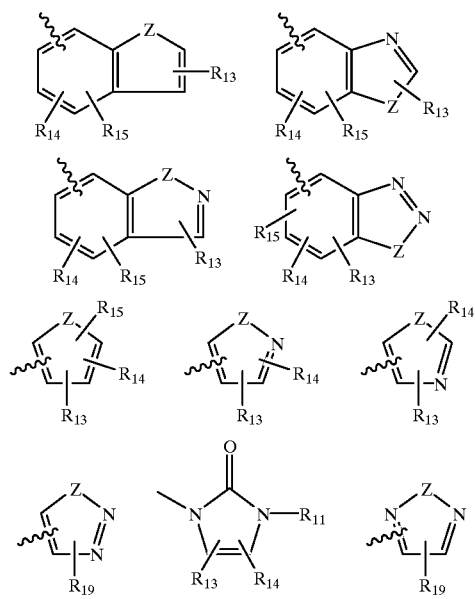

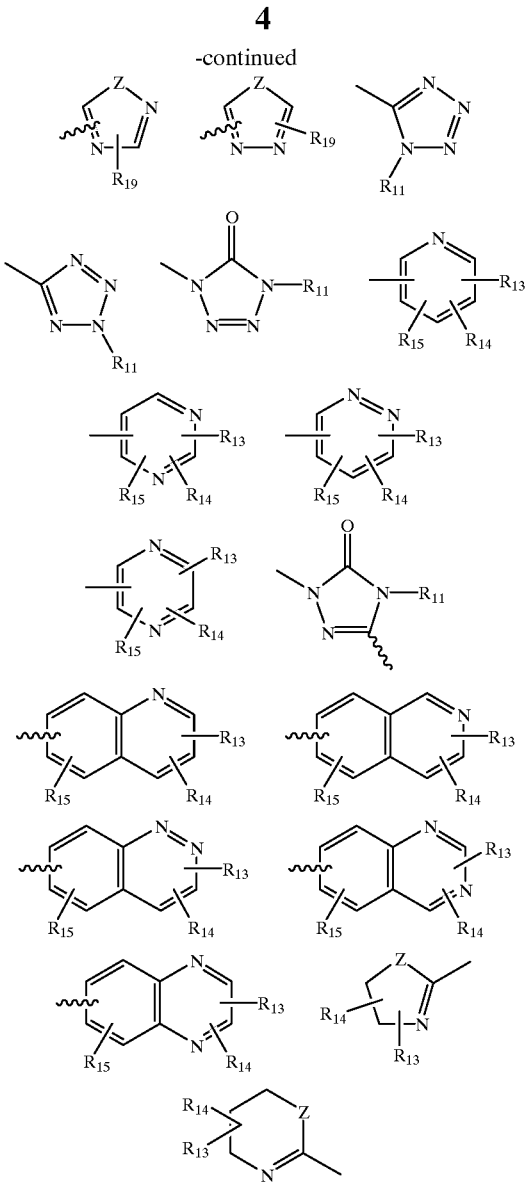

the nitrogen atoms contained in the $R_1$ heteroaromatic rings may exist either as drawn or, when chemically allowed, in their oxidized (N→O) state;

$R_2$ is heteroaryl, substituted heteroaryl, $C_1-C_6$ heteroaralkyl, $C_1-C_6$ substituted heteroaralkyl;

$R_2$ and A can optionally be taken together to form a ring of 5–7 atoms;

$R_3$, $R_4$ and $R_5$ are independently hydrogen, $C_1-C_6$ alkyl, substituted $C_1-C_6$ alkyl, $C_2-C_6$ alkenyl, substituted $C_2-C_6$ alkenyl, CN, nitro, $C_1-C_3$ perfluoroalkyl, $C_1-C_3$ perfluoroalkoxy, aryl, substituted aryl, aralkyl, substituted aralkyl, $R_{11}O(CH_2)_p-$, $(CH_2)_pS(O)_nR_{17}$ or halogen; wherein $R_{17}$ is hydrogen, $C_1-C_6$ alkyl, $C_1-C_3$ perfluoroalkyl, aryl or substituted aryl; or $R_3$ and $R_4$ taken together form a carbocyclic ring of 3–7 carbon atoms or a heterocyclic ring containing 1–3 heteroatoms selected from N, O and S;

$R_6$ is hydrogen, $C_1-C_6$ alkyl, substituted $C_1-C_6$ alkyl, aryl, substituted aryl, $C_1-C_3$ perfluoroalkyl, CN, $NO_2$, halogen, $R_{16}O(CH_2)_p-$;

$R_7$ is hydrogen, $C_1-C_6$ alkyl, or substituted $C_1-C_6$ alkyl, unless X is hydrogen or halogen, then $R_7$ is absent;

$R_8$ is hydrogen, $C(O)OR_9$, $C(O)NR_{11}R_{12}$, $NR_{11R12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, a heterocyclic ring or bicyclic heterocyclic ring with from 1 to 4 heteroatoms selected from N, O or S which can be optionally substituted by $R_3$, $R_4$ and $R_5$, $C_1$–$C_6$ alkyl or substituted $C_1$–$C_6$ alkyl, unless X is hydrogen or halogen, then $R_8$ is absent; or $R_7$ and $R_8$ taken together form a heterocyclic ring containing one or more heteroatoms selected from N, O or S which can be optionally substituted by $R_3$, $R_4$ and $R_5$; or $R_7$ and $R_8$ taken together form a carbocyclic ring of 3–7 atoms or

when m≠0;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together form a carbocyclic ring of 3–7 atoms or

when m≠0;

$R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ when taken together form a carbocyclic ring of 3–7 carbon atoms or a heterocyclic ring containing one or more heteroatoms when m≠0; or $R_9$ and $R_2$ taken together form a heterocyclic ring containing 3–7 carbon atoms and one or more heteroatoms when m≠0; or $R_{10}$ and $R_2$ taken together form a heterocyclic ring containing 3–7 carbon atoms and one or more heteroatoms;

$R_{11}$ and $R_{12}$ are independently a bond, hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{11}$ and $R_{12}$ when taken together can form an optionally substituted ring of 3–9 atoms;

$R_{13}$ is hydrogen, OH, $NR_7R_8$, $NR_{16}SO_2(C_1$–$C_6$ alkyl), $NR_{16}SO_2($substituted $C_1$–$C_6$ alkyl), $NR_{16}SO_2($aryl), $NR_{16}SO_2($substituted aryl), $NR_{16}SO_2(C_1$–$C_3$ perfluoroalkyl); $SO_2NR_{16}(C_1$–$C_6$ alkyl), $SO_2NR_{11}$ (substituted $C_1$–$C_6$ alkyl), $SO_2NR_{11}($aryl), $SO_2NR_{16}$ (substituted aryl), $SO_2NR_{16}(C_1$–$C_3$ perfluoroalkyl); $SO_2NR_{16}(C(O)C_1$–$C_6$ alkyl); $SO_2NR_{16}(C(O)$-substituted $C_1$–$C_6$ alkyl); $SO_2NR_{16}(C(O)$-aryl); $SO_2NR_{16}(C(O)$-substituted aryl); $S(O)_n(C_1$–$C_6$ alkyl); $S(O)_n$(substituted $C_1$–$C_6$ alkyl), $S(O)_n$(aryl), $S(O)_n$(substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$ or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{16}O(CH_2)_p$—, $R_{16}C(O)O(CH_2)_p$—, $R_{16}OC(O)(CH_2)_p$—, —$(CH_2)_pS(O)_nR_{17}$, —$(CH_2)_pC(O)$ $N(R_{16})_2$ or halogen; wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{18}$ is hydrogen, $C_1$–$C_6$ alkyl, substituted $C_1$–$C_6$ alkyl, $C(O)OR_{16}$, $C(O)N(R_{16})_2$, $C(O)R_{16}$, $S(O)_nR_{16}$;

$R_{19}$ is either the definition of $R_{13}$ or $R_{14}$;

X is N, O, $S(O)_n$, C(O), $(CR_{11}R_{12})_p$, a single bond to $R_8$, $C_2$–$C_6$ alkenyl, substituted $C_2$–$C_6$ alkenyl, $C_2$–$C_6$ alkynyl, or substituted $C_2$–$C_6$ alkynyl; when X is O, $S(O)_n$, C(O), or $CR_{11}R_{12}$ only $R_8$ is possible.

Z is O, S or $NR_{11}$ m is 0, 1, 2 or 3;

n is 0, 1 or 2;

p is 0, 1, 2, 3 or 4; and the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

In a preferred embodiment, there are disclosed compounds of formula I wherein

A is $C_1$–$C_6$ alkyl, substituted $C_1$–$C_6$ alkyl or $C_0$–$C_5$ alkyl-$S(O)_n$-$C_0$-$C_5$ alkyl;

$R_0$ is hydrogen;

$R_1$ is

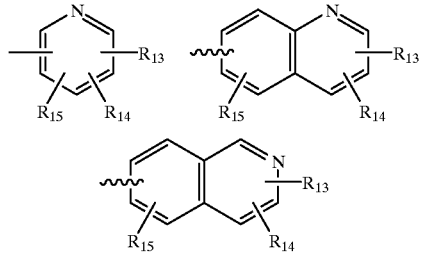

the nitrogen atoms contained in the $R_1$ heteroaromatic rings may exist either as drawn or, when chemically allowed, in their oxidized (N→O) state;

$R_3$, $R_4$ and $R_5$ are independently hydrogen, $C_1$–$C_6$ alkyl, substituted $C_1$–$C_6$ alkyl or halogen;

$R_8$ is $C(O)NR_{11}R_{12}$, or $R_{11}$ and $R_{12}$ are independently a bond, hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{11}$ and $R_{12}$ when taken together can form an optionally substituted ring of 3–9 atoms;

X is $(CR_{11}R_{12})_p$;

or a pharmaceutically acceptable addition salt and/or hydrate thereof, or where applicable, a geometric or optical isomer or racemic mixture thereof.

Preferred substituents when $R_{11}$ and $R_{12}$ are taken together include 7-aza-bicyclo[2.2.1]heptane and 2-aza-bicyclo[2.2.2] octane.

Unless otherwise stated or indicated, the following definitions shall apply throughout the specification and claims.

When any variable (e.g., aryl, heterocycle, $R_1$, etc.) occurs more than one time in any constituent or in formula I, its definition on each occurrence is independent of its definition at every other occurrence. Also, combinations of substituents and/or variables are permissible only if such combinations result in stable compounds.

The term "alkyl" is intended to include both branched- and straight-chain saturated aliphatic hydrocarbon groups having the specified number of carbon atoms, e.g., methyl (Me), ethyl (Et), propyl, butyl, pentyl, hexyl, heptyl, octyl, nonanyl, decyl, undecyl, dodecyl, and the isomers thereof such as isopropyl (i-Pr), isobutyl (i-Bu), sec-butyl (s-Bu), tert-butyl (t-Bu), isopentane, isohexane, etc.

The term "aryl" includes phenyl and naphthyl. Preferably, aryl is phenyl.

The term "heteroaryl" is intended to include the compounds shown below:

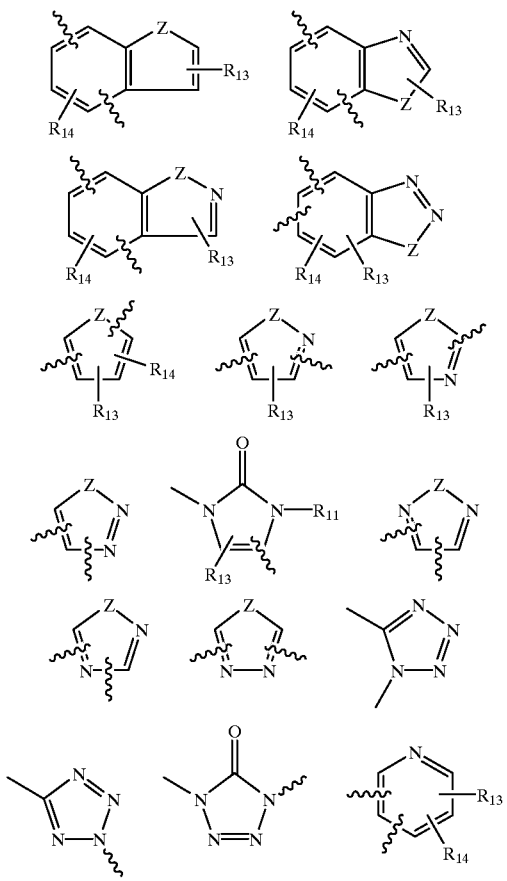

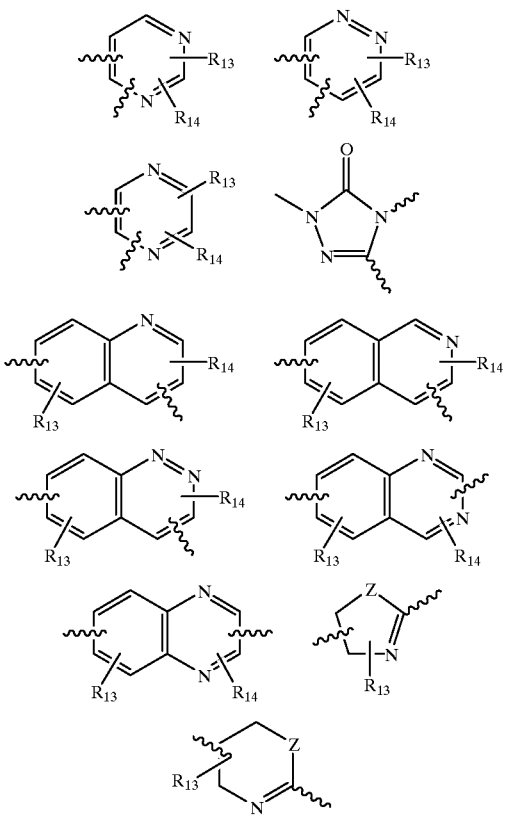

where Z is O, S, or $NR_{11}$, as well as the following compounds:

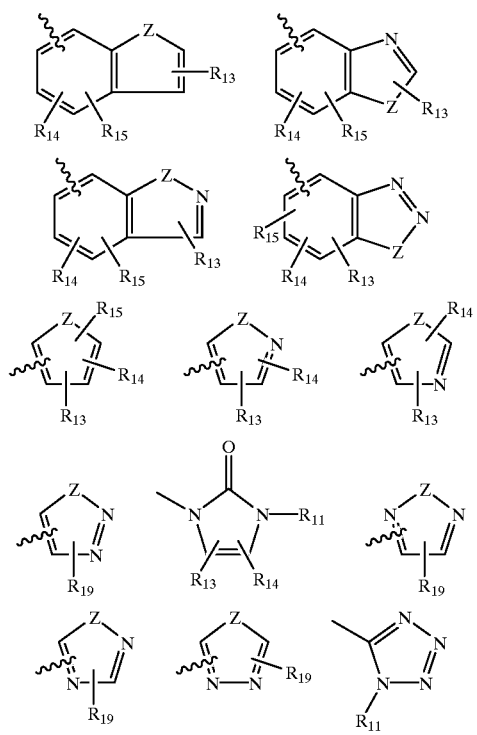

-continued

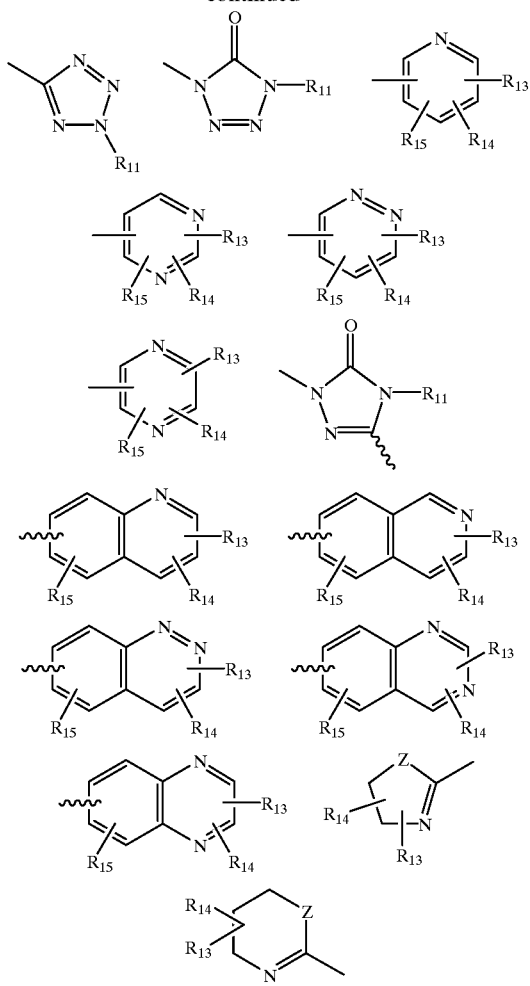

The term "halogen" or "halo" is intended to include fluorine, chlorine, bromine and iodine.

The term "heterocycle" or "heterocyclic ring" is defined by all non-aromatic, heterocyclic rings of 3–7 atoms containing 1–3 heteroatoms selected from N, O, and S, such as oxirane, oxetane, tetrahydrofuran, tetrahydropyran, pyrrolidine, piperidine, tetrahydropyridine, tetrahydropyrimidine, tetrahydrothiophene, tetrahydrothiopyran, morpholine, hydantoin, valerolactam, pyrrolidinone, and the like.

As used herein, the term "composition" is intended to encompass a product comprising the specified ingredients in the specified amounts, as well as any product which results, directly or indirectly, from combination of the specified ingredients in the specified amounts.

In addition, it is well known to those skilled in the art that many of the foregoing heterocyclic groups can exist in more than one tautomeric form. It is intended that all such tautomers be included within the ambit of this invention.

The optical isomeric forms, that is mixtures of enantiomers, e.g., racemates, or diastereomers as well as individual enantiomers or diastereomers of the instant compound are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diastereomers and then recovering the desired isomer. In addition, the individual optical isomers may be prepared by asymmetric synthesis.

Additionally, a given chemical formula or name shall encompass pharmaceutically acceptable addition salts thereof and solvates thereof, such as hydrates.

The compounds of the present invention, while effective themselves, may be formulated and administered in the form of their pharmaceutically acceptable addition salts for purposes of stability, convenience of crystallization, increased solubility and other desirable properties.

The compounds of the present invention may be administered in the form of pharmaceutically acceptable salts. The term "pharmaceutically acceptable salt" is intended to include all acceptable salts. Examples of acid salts are hydrochloric, nitric, sulfuric, phosphoric, formic, acetic, trifluoroacetic, propionic, maleic, succinic, malonic, methane sulfonic and the like which can be used as a dosage form for modifying the solubility or hydrolysis characteristics or can be used in sustained release or prodrug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, e.g. by reacting a free acid with a suitable organic or inorganic base, or alternatively by reacting a free base with a suitable organic or inorganic acid.

Also, in the case of an acid (—COOH) or alcohol group being present, pharmaceutically acceptable esters can be employed, e.g. methyl, ethyl, butyl, acetate, maleate, pivaloyloxymethyl, and the like, and those esters known in the art for modifying solubility or hydrolysis lcharacteristics for use as sustained release or prodrug formulations.

The compounds of the present invention may have chiral centers other than those centers whose stereochemistry is depicted in formula I, and therefore may occur as racemates, racemic mixtures and as individual enantiomers or diastereomers, with all such isomeric forms being included in the present invention as well as mixtures thereof. Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

The compounds of the invention are prepared by the following reaction schemes. All substituents are as defined above unless indicated otherwise.

Scheme A

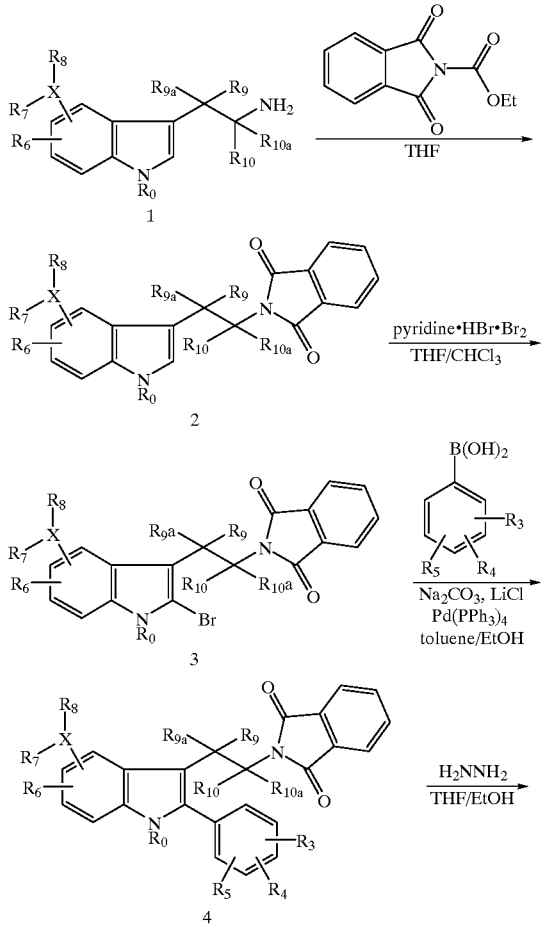
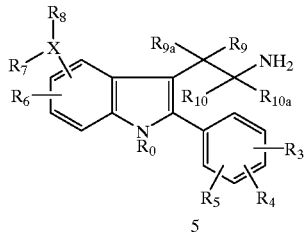

Reaction Scheme A

As shown in reaction Scheme A, treatment of tryptamine (1) with N-carboxyphthalimide in an inert organic solvent such as tetrahydrofuran at a temperature of 20–65° C., preferably 65° C., for a period of 12–48 hours gives the corresponding N-phthalimidotryptamine derivative (2). The N-phthalimidotryptamine (2) could be further modified by treatment with a brominating agent such as pyridinium hydrobromide perbromide, pyrrolidone hydrotribromide, or the like in an inert organic solvent such as tetrahydrofuran, methylene chloride, chloroform, or mixtures thereof at 0–25° C. for a period of 30 minutes to 4 hours to provide the 2-bromotryptamine (3). Bromide (3) may be reacted with an arylboronic acid (prepared essentially as described in: Gronowitz, S.; Hornfeldt, A.-B.; Yang, Y.-H. *Chem. Scr.* 1986, 26, 311–314.) with palladium (0) catalysis, a weak base such as aqueous sodium carbonate or the like, and a chloride source such as lithium chloride in an inert solvent like toluene, benzene, ethanol, propanol or mixtures thereof at a temperature of 25°–100° C., preferably 80° C., for a period of 1–6 hours to give the 2-aryltryptamine derivative (4). Finally, the phthalimido group may be removed by treatment of (4) with aqueous hydrazine in an inert solvent such as methanol or ethanol at a temperature of 0°–25° C. for a period of 4–24 hours to give tryptamine (5).

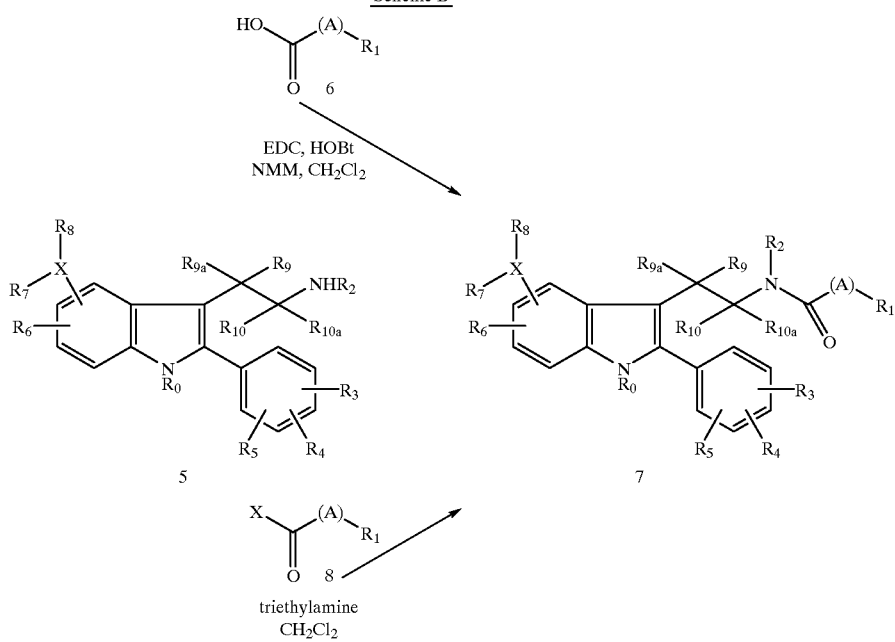

Reaction Scheme B

As shown in reaction Scheme B, the 2-aryltryptamine may be condensed with a carboxylic acid of type (6) using the coupling reagent 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours to provide the corresponding amide derivative (7). Alternatively, 2-aryltryptamine (5) can be treated with an active ester or acid chloride of type (8) in an inert organic solvent such as methylene chloride, chloroform, tetrahydrofuran, diethyl ether, or the like and a tertiary amine base such as triethylamine, diisopropylethylamine, pyridine or the like at a temperature of 0°–25° C. for 30 minutes to 4 hours to give (7).

Reaction Scheme C

As shown in reaction Scheme C, the amide carbonyl of (7) can be reduced by treatment with borane, lithium aluminum hydride, or equivalent hydride sources in an inert organic solvent such as tetrahydrofuran, diethyl ether, 1,4-dioxane or the like at 25°–100° C., preferably 65° C., for a period of 1–8 hours to give the corresponding amine compound (9).

Reaction Scheme D

As shown in reaction Scheme D, the 2-aryltryptamine (23 or 5) can be modified by treatment with an aldehyde or ketone of type (10) in the presence of a weak acid such as trifluoroacetic acid (TFA), acetic acid or the like, with or without a dessicant such as 3Å molecular sieves or magnesium sulfate, and a hydride source such as sodium borohydride or sodium cyanoborohydride, in an inert organic solvent such as methanol, ethanol, isopropanol, tetrahydrofuran, dichloromethane, chloroform, or mixtures thereof at a temperature of 0°–25° C. for a period of 1–12 hours to give the corresponding secondary or tertiary amine derivative (11).

Scheme E

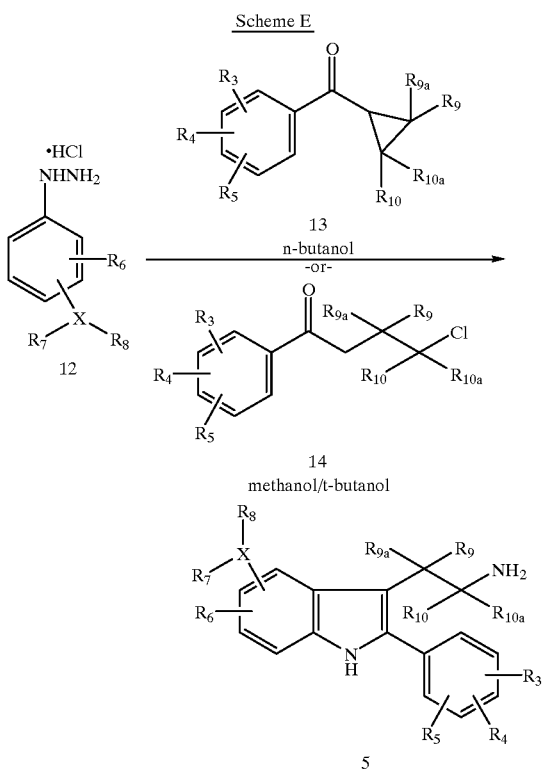

Reaction Scheme E

As shown in reaction Scheme E, treatment of an arylhydrazine or arylhydrazine hydrochloride (12) with an arylcyclopropylketone of type (13) in a polar organic solvent such as methanol, ethanol, n-propanol, isopropanol, n-butanol, t-butanol, preferably n-butanol, at a temperature of 70°–120° C. for a period of 8–24 hours gives 2-aryltryptamine (5). Alternatively, when an arylhydrazine or arylhydrazine hydrochloride (12) is treated with an arylbutyl ketone of type (14) containing a leaving group (chloride, bromide, iodide, O-methansulfonate, O-trifluoromethansulfonate, or the like) at the 4-position in a polar solvent such as methanol, ethanol, n-propanol, isopropanol, n-butanol, t-butanol, or mixtures thereof at room temperature for a period of 30 minutes to 2 hours followed by heating to a temperature of 65°–100° C. for 4–24 hours, 2-aryltryptamine (5) is produced.

Scheme F

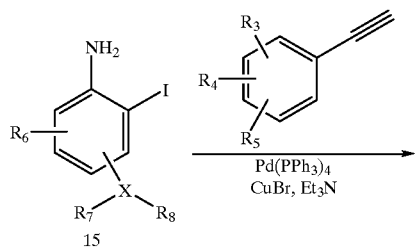

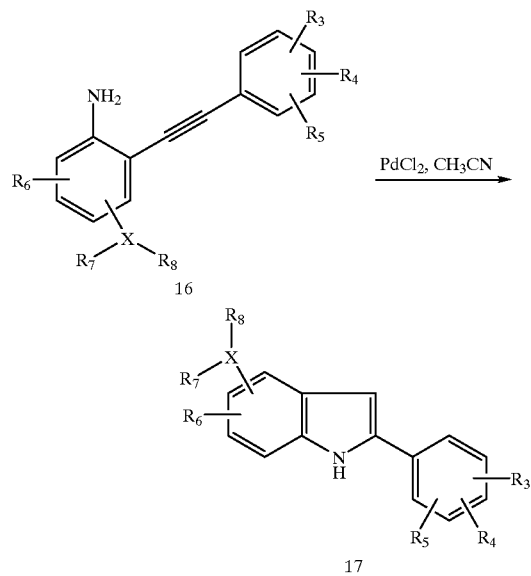

Reaction Scheme F

As shown in reaction Scheme F, iodoanilines of type (15) may be reacted with aryl acetylenes, an appropriate palladium (0) catalyst such as tetrakis(triphenylphosphine) palladium, a copper (I) halide such as cuprous bromide in an inert organic solvent such as triethylamine at a temperature of 50°–88° C. for a period of 30 minutes to 5 hours to provide the diarylacetylene (16). Acetylene (16) may be further modified by treatment with a palladium (II) catalyst such as palladium (II) chloride or palladium (II) acetate in an inert organic solvent such as acetonitrile at a temperature of 50°–82° C. for a period of 30 minutes to 6 hours to give 2-arylindole (17).

Scheme G

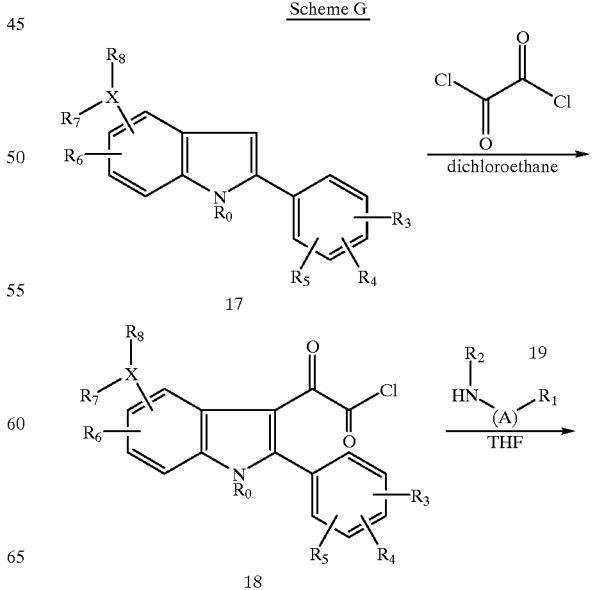

-continued

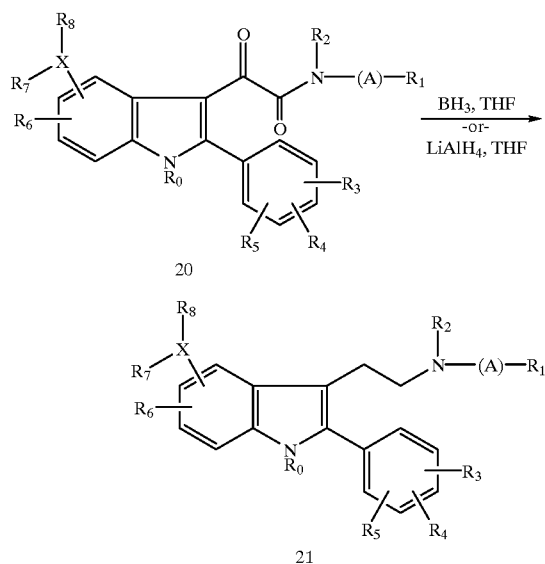

Reaction Scheme G

As shown in reaction Scheme G. treatment of 2-arylindole (17) with oxalyl chloride neat or in an inert organic solvent such as methylene chloride, chloroform, dichloroethane, tetrahydrofuran or the like at a temperature of 25°–65° C. for a period of 3–24 hours gives the acylchloride adduct (18). The crude product (18) may be reacted with an amine of type (19) in an inert organic solvent such as diethylether, tetrahydrofliran, methylene chloride, chloroform or the like and an amine base such as triethylamine, duisopropylethylamine or pyridine at a temperature of 0°C.–25° C. for a period of 30 minutes to 4 hours to provide the amide derivative (20). Amide (20) may be further modified by treatment with a reducing agent such as borane or lithium aluminum hydride in an inert organic solvent such as tetrahydrofuran at elevated temperatures, preferably reflux, for a period of 1–5 hours to give compound (21).

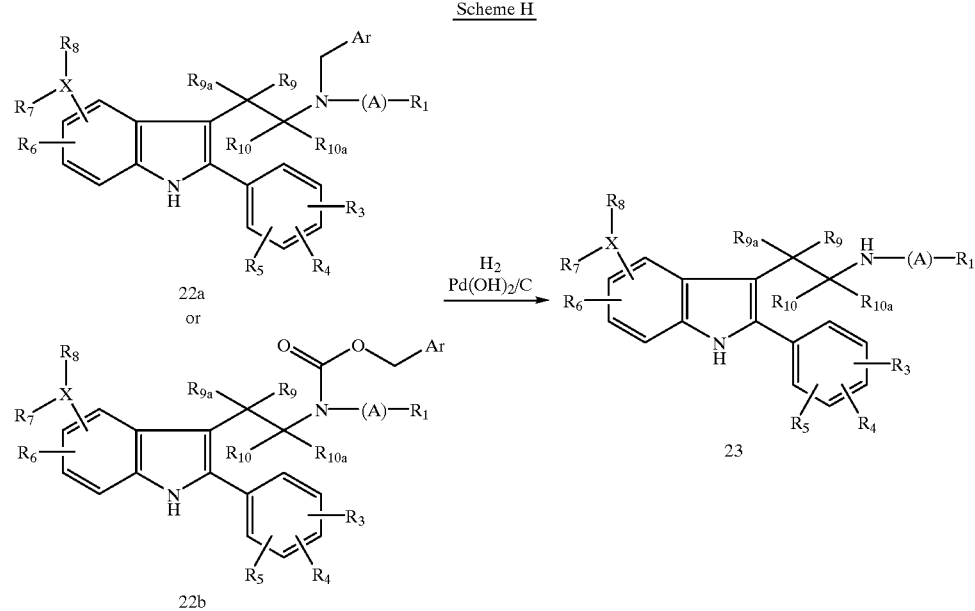

Scheme H

Scheme H

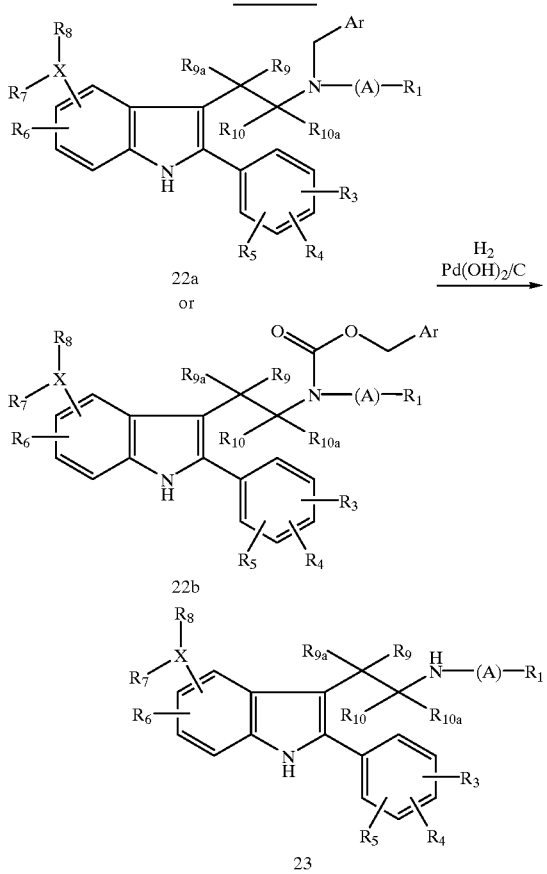

Reaction Scheme H

As shown in reaction Scheme H, N-benzyl derivatives of type (22a) or N-benzyloxycarbonyl derivatives of type (22b) may be reduced to provide the secondary amine analogs (7) by treatment with hydrogen (1 atm) and an appropriate catalyst such as palladium on carbon, palladium hydroxide on carbon, or the like in an inert organic solvent such as tetrahydrofuran, ethyl acetate, methanol, ethanol, or mixtures thereof to which has been added a weak acid such as 30% aqueous acetic acid for a period of 10 minutes to 3 hours or until the aryl group has been removed to give the secondary amine.

Scheme I

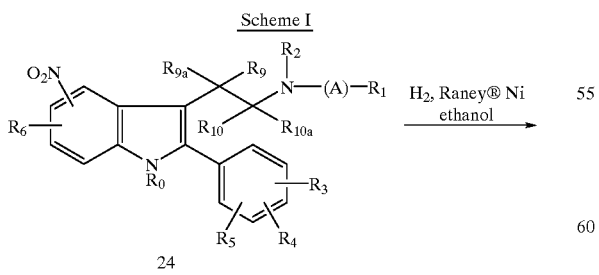

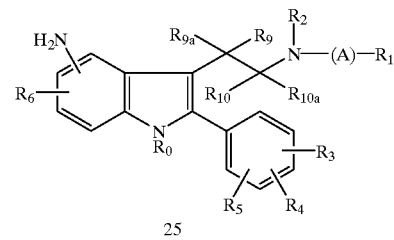

Reaction Scheme I

As shown in reaction Scheme I, treatment of a nitroindole of type (24) with hydrogen (1 atm) and an appropriate catalyst such as Raney® Nickel in an inert organic solvent such as ethanol, methanol, or the like at room temperature for a period of 2–12 hours gives the corresponding aminoindole derivative (25).

Scheme J

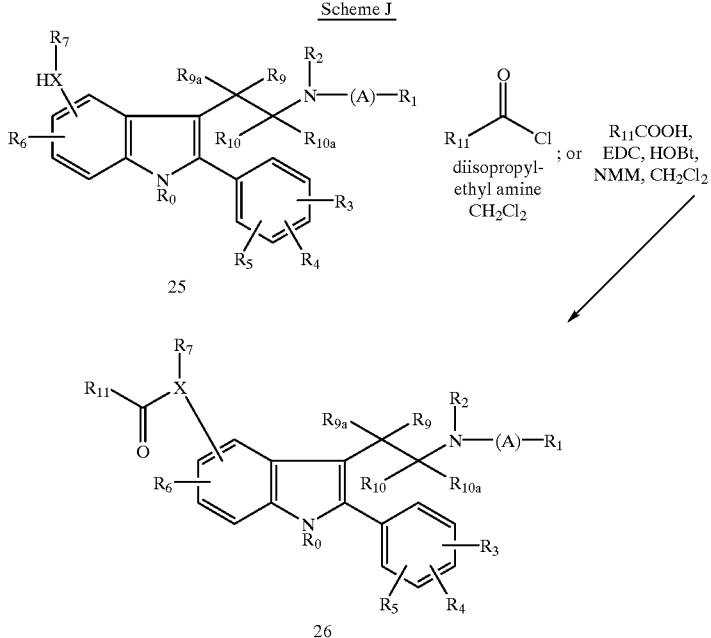

Reaction Scheme J

As shown in reaction Scheme J, amino- or hydroxyindole (25) may be modified by acylation under a variety of conditions. For example, treatment of (25) with an acid chloride, acid anhydride or active ester and an amine base such as triethylamine, diisopropylethylamine, pyridine, or the like in an inert organic solvent such as methylene chloride, chloroform, tetrahydrofuran, or mixtures thereof at 0° C. to room temperature for a period of 1 to 12 hours gives the corresponding amide or ester derivatives (26). Alternatively (25) may be coupled with a carboxylic acid by one of the many dehydrating agents commonly employed. For instance, treatment of aminoindole (25) with an appropriate carboxylic acid and 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, dimethylformamide, or mixtures thereof at or near room temperature for a period of 3–24 hours provides the corresponding amide or ester derivative (26).

Scheme K

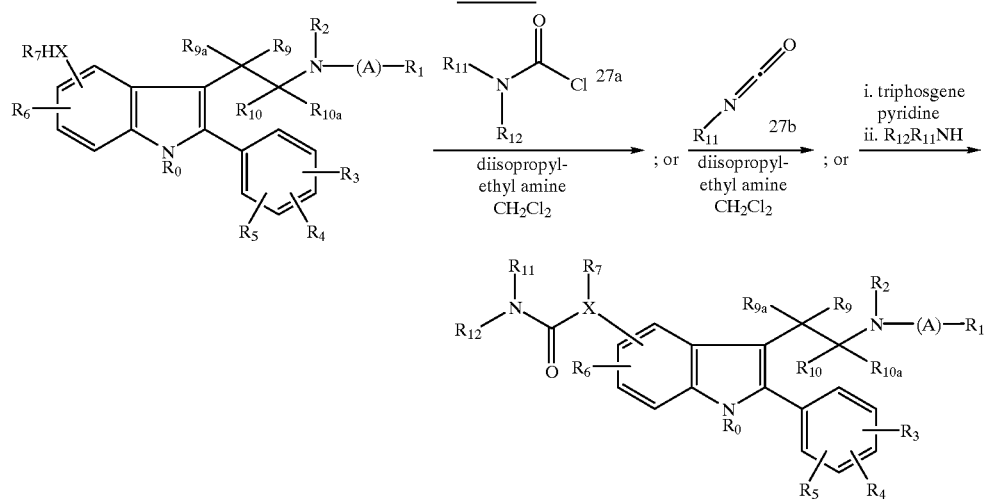

Reaction Scheme K

As shown in reaction Scheme K, urea or carbamate derivatives of (25) can be prepared by treatment with a carbamoyl chloride of type (27a), or alternatively with an isocyanate reagent of type (27b), and an amine base such as pyridine, triethylamine, diisopropylethylamine, N-methylmorpholine or the like in an inert organic solvent such as methylene chloride, chloroform, dimethylformamide, tetrahydrofuran or mixtures thereof at a temperature of 0°–65° C. for a period of 1–72 hours to give (28). Compound (25) can also be modified by treatment with a bis(electrophilic) reagent such as phosgene, triphosgene, 1,1'-carbonyldiimidazole, N,N'-disuccinimidyl carbonate, or the like with or without the addition of an amine base such as pyridine, triethylamine, diisopropylethylamine, N-methylmorpholine in an inert solvent such as methylene chloride, chloroform, or the like at a temperature of –20°–0° C. for a period of 20 minutes to 2 hours. After this time, the reaction mixture is treated with an appropriate mono- or disubstituted amine at –20° to 25° C. for a period of 1–5 hours to give the urea or carbamate analog (28).

Reaction Scheme L

As shown in reaction Scheme L, amine (25) can be modified by treatment with an appropriate sulfonyl chloride of type (29) or sulfamyl chloride of type (30) with an amine base such as pyridine, triethylamine, diisopropylethylamine, N-methylmorpholine in an inert solvent such as methylene chloride, chloroform, dichloroethane or the like at a temperature of –20°–25° C. for a period of 20 minutes to 2 hours to give the corresponding N-sulfonamide (31) or N-sulfamylamide (32) derivatives, respectively.

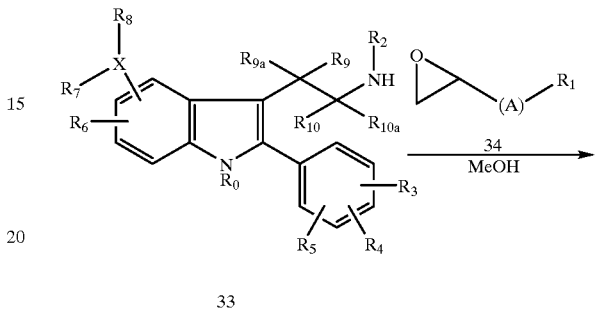

Scheme M

33

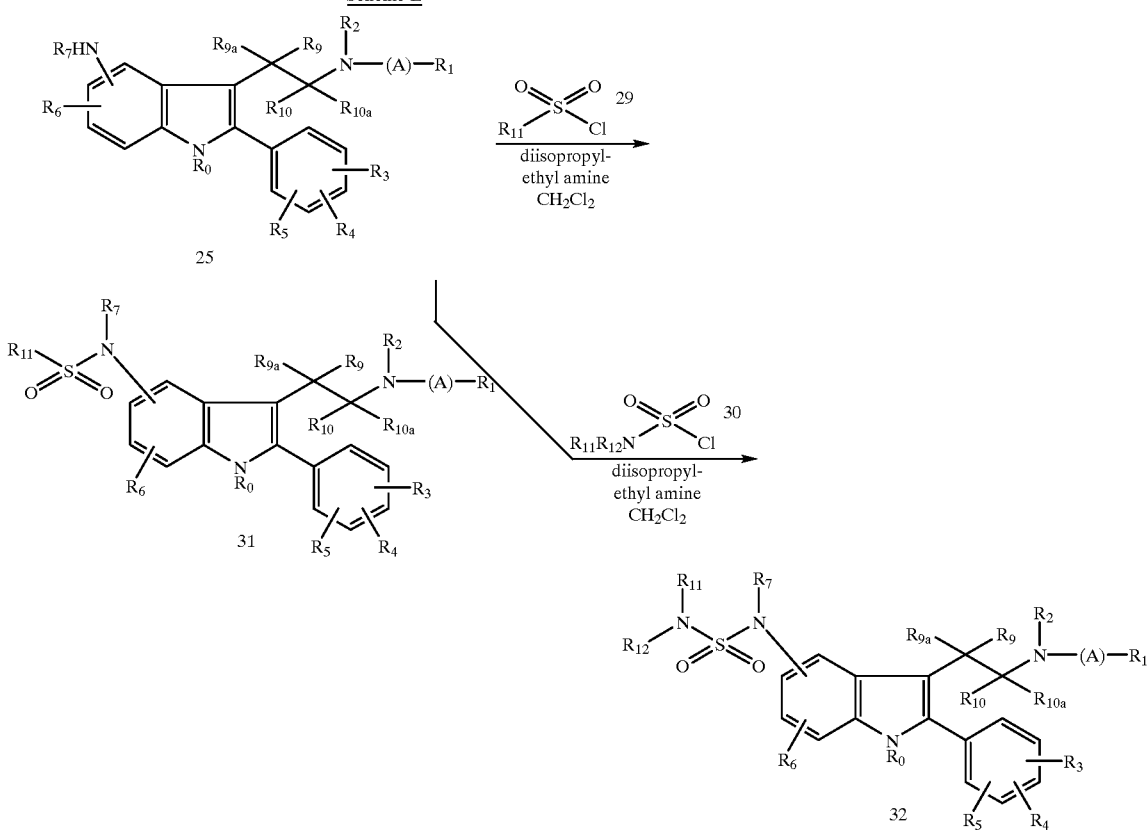

Scheme L

25

31

32

25
-continued

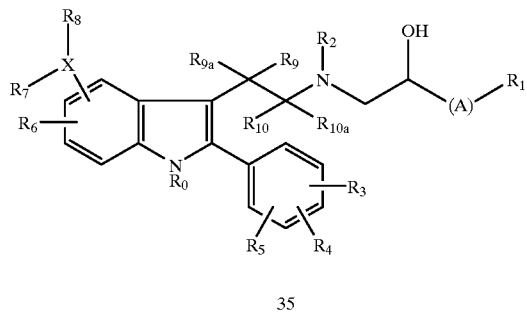

35

Reaction Scheme M

As shown in reaction Scheme M, the 2-aryltryptamine (33) can be modified by treatment with an epoxide such as (34) in an inert organic solvent such as methanol, ethanol, isopropanol, butanol, tert-butanol, mixtures thereof at a temperature of 65°–110° C. for a period of 8–20 hours to give the corresponding amino-alcohol derivative (35).

26
Reaction Scheme N

As shown in reaction Scheme N, amide derivatives of an acid-containing indole derivative such as (36) can be prepared by treatment with an appropriate amine ($R_{12}R_{11}NH$) and a suitable coupling agent such as benzotriazol-1-yloxy-tris(pyrrolidino) phosphonium hexafluorophosphate (PyBOP), benzotriazol-1-yloxy-tris(dimethylamino) phosphonium hexafluorophosphate (BOP), 1-(3-dimethylaminopropyl)-3-ethylcarbodiimide hydrochloride (EDC), 1,3-dicyclohexylcarbodiimide (DCC) or the like with or without 1-hydroxybenzotriazole (HOBt) and a tertiary amine base such as N-methylmorpholine (NMM), triethylamine or the like in an inert organic solvent such as methylene chloride, chloroform, tetrahydrofuran, dimethylformamide, or mixtures thereof at or near room temperature for a period of 3 hours to 7 days provides the corresponding amide derivative (37).

Scheme N

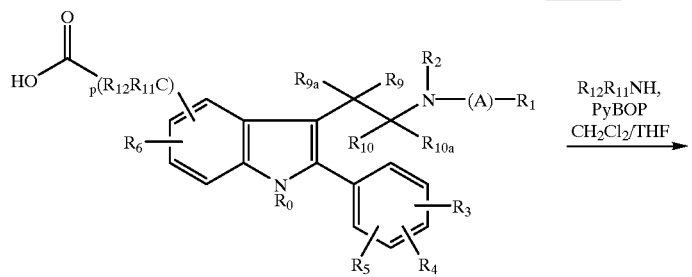

36

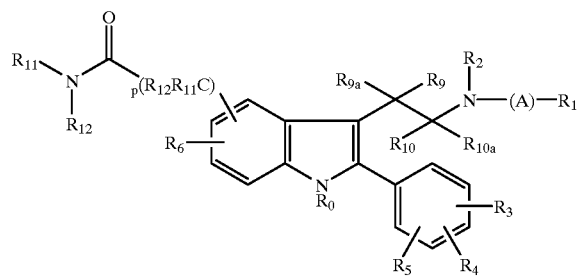

37

Scheme O

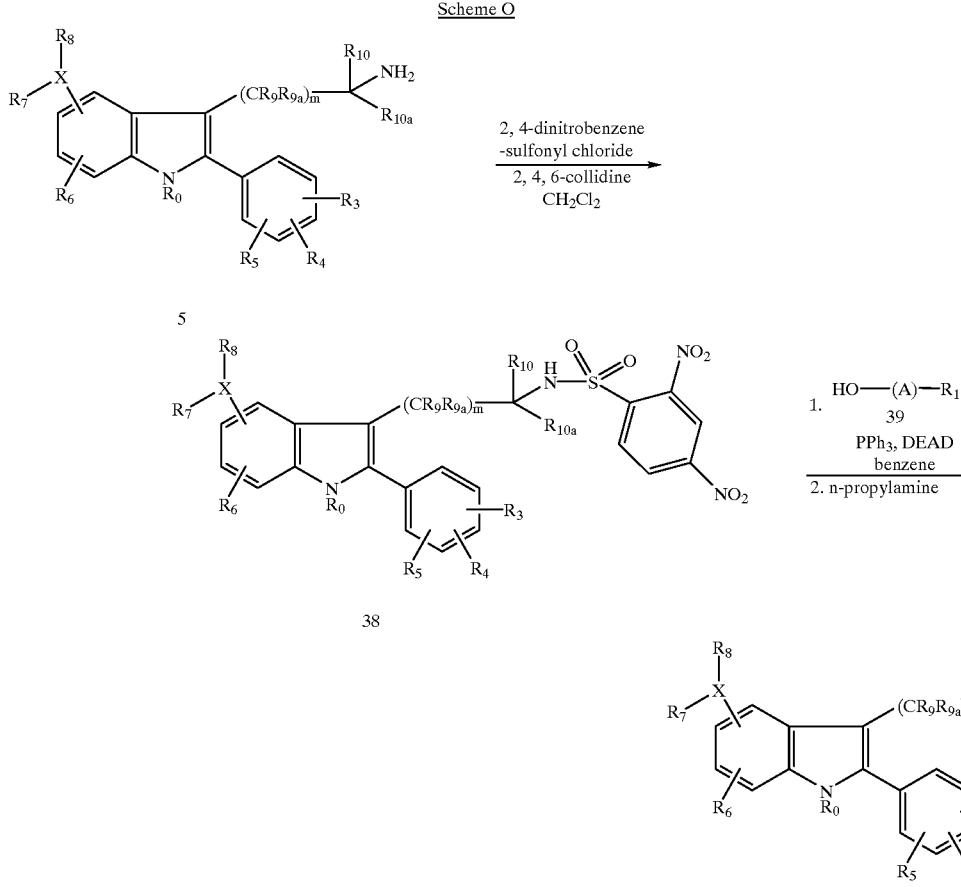

Reaction Scheme O

As shown in reaction Scheme O, the tryptamine 5 can be modified by reaction with an arylsufonyl chloride such as 2-nitrobenzenesulfonyl chloride, 4-nitrobenzenesulfonyl chloride or 2,4-dinitrobenzenesulfonyl chloride and a hindered amine base such as 2,4,6-collidine, 2,6-lutidine or the like in an inert organic solvent such as methylene chloride to provide the corresponding sulfonamide 38. Sulfonamides such as 38 can be further modified by reaction with an alcohol of type 39 in the presence of triphenylphosphine and an activating agent such as diethyl azodicarboxylate (DEAD), diisopropyl azodicaboxylate or the like in an inert organic solvent such as benzene, toluene, tetrahydrofuran or mixtures thereof to give the dialkylsulfonamide adduct. Removal of the sulfonyl group is accomplished by treatment with a nucleophilic amine such as n-propylamine or the like in an inert organic solvent such as methylene chloride to give secondary amines of type 23.

The compounds of the present invention are useful in the treatment of various sex-hormone related conditions in men and women. This utility is manifested in their ability to act as antagonists of the neuropeptide hormone GnRH as demonstrated by activity in the following in vitro assays.

Human GnRH receptor binding assay

Crude membranes prepared from CHO cells expressing human GnRH receptors were the sources for GnRH receptor. [$^{125}$I]Buserelin (a peptidyl GnRH analog) was used as the radiolabelled ligand. The binding activity was determined as an $IC_{50}$ which is the antagonist concentration required to inhibit the specific binding of [$^{125}$I]buserelin to GnRH receptors by 50%.

Rat pituitary GnRH receptor binding assay:

Crude plasma membranes prepared from rat pituitary tissues were incubated in a Tris.HCl buffer (50 mM, PH. 7.5) containing bovine serum albumin (0.1%), [I-125]D-t-Bu-Ser6-Pro9-ethyl amide-GnRH, and the desired concentration of a test compound. The assay mixtures were incubated at 4° C. for 90–120 minutes followed by rapid filtration and repeated washings through a glass fiber filter. The radioactivity of membrane bound radioligands was determined in a gamma-counter. From this data, the $IC_{50}$ of the radioligand binding to GnRH receptors in the presence of test compound was estimated.

Inhibition of LH release assay:

Active compounds from the GnRH receptor binding assay were further evaluated with an in vitro LH release assay to confirm their antagonist activity (blocking GnRH-induced LH release).

1. Sample Preparation

The compounds to be assayed were dissolved and diluted in DMSO. The final concentration of DMSO in the incubation medium was 0.5%.

2. Assay

The Wistar male rats (150–200 grams) were obtained from Charles River Laboratories (Wilmington, Mass.). Rats were maintained at a constant temperature (250° C.) on a 12-hr light, 12-hr dark cycle. Rat chow and water were available ad libitum. The animals were sacrificed by decapitation and pituitary glands were aseptically removed and placed in Hank's Balanced Salt Solution (HBSS) in a 50-mL polypropylene centrifuge tube. The collection tube was centrifuged for 5 min at 250×g, and HBSS was removed by aspiration. Pituitary glands were transferred to a disposable petri plate and minced with a scalpel. The minced tissue was then transferred to a 50-mL disposable centrifuge tube by suspending the tissue fragments in three successive 10-mL aliquots of HBSS containing 0.2% collagenase and 0.2% hyaluronidase. The cell dispersion was carried out in a water bath at 37° C. with gentle stirring for 30 min. At the end of the incubation, the cells were aspirated 20 to 30 times with a pipet and the undigested pituitary fragments were allowed to settle for 3 to 5 min. The suspended cells were removed by aspiration, and then subjected to a 1200×g centrifugation for 5 min. The cells were then resuspended in Culture medium. The undigested pituitary fragments were treated with 30 mL aliquots of the digestion enzymes as above for a total of 3 digestions with the collagenase/hyaluronidase mixture. The resulting cell suspensions were pooled, counted and diluted to a concentration of $3 \times 10^5$ cells/ml, and 1.0 ml of this suspension was placed in each well of a 24-well tray (Costar, Cambridge, Mass.). Cells were maintained in a humidified 5% $CO_2$-95% air atmosphere at 37° C. for 3 to 4 days. The culture medium consisted of DMEM containing 0.37% $NaHCO_3$, 10% horse serum, 2.5% fetal bovine serum, 1% non-essential amino acids, 1% glutamine, and 0.1% gentamycin. On the day of an experiment, cells were washed three times 1½ hrs prior to and two more times immediately before the start of the experiment with DMEM containing 0.37% $NaHCO_3$, 10% horse serum, 2.5% fetal bovine serum, 1% non-essential amino acids(100×), 1% glutamine(100×), 1% Penicillin/Streptomycin(10,000 Units of Penicillin and 10,000 micrograms of Streptomycin per ml), and 25 mM HEPES, pH 7.4. LH release was initiated by adding 1 ml of fresh medium containing test compounds in the presence of 2 nM GnRH to each well in duplicate. Incubation was carried out at 37° C. for 3 hr. After incubation, medium was removed and centrifuged at 2,000×g for 15 min to remove any cellular material. The supernatant fluid was removed and assayed for LH content with a double antibody RIA procedure using materials obtained from Dr. A. F. Parlow (Harbor-UCLA Medical Center, Torrance, Calif.).

The compounds of formula I are useful in a number of areas affected by GnRH. They may be useful in sex-hormone related conditions, sex-hormone dependent cancers, benign prostatic hypertrophy or myoma of the uterus. Sex-hormone dependent cancers which may benefit from the administration of the compounds of this invention include prostatic cancer, uterine cancer, breast cancer and pituitary gonadotrophe adenomas. Other sex-hormone dependent conditions which may benefit from the administration of the compounds of this invention include endometriosis, polycystic ovarian disease, uterine fibroids and precocious puberty. The compounds may also be used in combination with an angiotensin-converting enzyme inhibitor such as Enalapril or Captopril, an angiotensin II-receptor antagonist such as Losartan or a renin inhibitor for the treatment of uterine fibroids.

The compounds of the invention may also be useful for controlling pregnancy, as a contraceptive in both men and women, for in vitro fertilization, in the treatment of premenstrual syndrome, in the treatment of lupus erythematosis, in the treatment of hirsutism, in the treatment of irritable bowel syndrome and for the treatment of sleep disorders such as sleep apnea.

A further use of the compounds of this invention is as an adjunct to growth hormone therapy in growth hormone deficient children. The compounds may be administered with growth hormone or a compound which increases the endogenous production or release of growth hormone. Certain compounds have been developed which stimulate the release of endogenous growth hormone. Peptides which are known to stimulate the release of endogenous growth hormone include growth hormone releasing hormone, the growth hormone releasing peptides GHRP-6 and GHRP-1 (described in U.S. Pat. No. 4,411,890, PCT Patent Pub. No. WO 89/07110, and PCT Patent Pub. No. WO 89/07111) and GHRP-2 (described in PCT Patent Pub. No. WO 93/04081), as well as hexarelin (*J. Endocrinol Invest.*, 15(Suppl 4), 45 (1992)). Other compounds which stimulate the release of endogenous growth hormone are disclosed, for example, in the following: U.S. Pat. No. 3,239,345; U.S. Pat. No. 4,036,979; U.S. Pat. No. 4,411,890; U.S. Pat. No. 5,206,235; U.S. Pat. No. 5,283,241; U.S. Pat. No. 5,284,841; U.S. Pat. No. 5,310,737; U.S. Pat. No. 5,317,017; U.S. Pat. No. 5,374,721; U.S. Pat. No. 5,430,144; U.S. Pat. No. 5,434,261; U.S. Pat. No. 5,438,136; EPO Patent Pub. No. 0,144,230; EPO Patent Pub. No. 0,513,974; PCT Patent Pub. No. WO 94/07486; PCT Patent Pub. No. WO 94(08583; PCT Patent Pub. No. WO 94/11012; PCT Patent Pub. No. WO 94/13696; PCT Patent Pub. No. WO 94/19367; PCT Patent Pub. No. WO 95/03289; PCT Patent Pub. No. WO 95/03290; PCT Patent Pub. No. WO 95/09633; PCT Patent Pub. No. WO 95/11029; PCT Patent Pub. No. WO 95/12598; PCT Patent Pub. No. WO 95/13069; PCT Patent Pub. No. WO 95/14666; PCT Patent Pub. No. WO 95/16675; PCT Patent Pub. No. WO 95/16692; PCT Patent Pub. No. WO 95/17422; PCT Patent Pub. No. WO 95/17423; *Science*, 260, 1640–1643 (Jun. 11, 1993); *Ann. Rep. Med. Chem.*, 28, 177–186 (1993); *Bioorg. Med. Chem. Ltrs.*, 4(22),2709–2714 (1994); and *Proc. Natl. Acad. Sci. USA* 92, 7001–7005 (July 1995).

Representative preferred growth hormone secretagoues employed in the present combination include the following:

1) N-[1(R)-[(1,2-Dihydro-1-methanesulfonylspiro[3H-indole-3,4'-piperidin]-1'-yl)carbonyl]-2-(1H-indol-3-yl) ethyl]-2-amino-2-methylpropanamide;
2) N-[1(R)-[(1,2-Dihydro-1-methanecarbonylspiro[3H-indole-3,4'-piperidin]-1'-yl)carbonyl]-2-(H-indol-3-yl) ethyl]-2-amino-2-methylpropanamide;
3) N-[1(R)-[(1,2-Dihydro-1-benzenesulfonylspiro[3H-indole-3,4'-piperidin]-1'-yl)carbonyl]-2-(1H-indol-3-yl) ethyl]-2-amino-2-methylpropanamide;
4) N-[1(R)-[(3,4-Dihydro-spiro[2H-1-benzopyran-2,4'-piperidin]-1'-yl) carbonyl]-2-(1H-indol-3-yl)ethyl]-2-amino-2-methylpropanamide;

5) N-[1(R)-[(2-Acetyl-1,2,3,4-tetrahydrospiro[isoquinolin-4,4'-piperidin]-1'-yl)carbonyl]-2-(indol-3-yl)ethyl]-2-amino-2-methyl-propanamide;
6) N-[1(R)-[(1,2-Dihydro-1-methanesulfonylspiro[3H-indole-3,4'-piperidin]-1'-yl)carbonyl]-2-(phenylmethyloxy)ethyl]-2-amino-2-methylpropanamide;
7) N-[1(R)-[(1,2-Dihydro-1-methanesulfonylspiro[3H-indole-3,4'-piperidin]-1'-yl)carbonyl]-2-(phenylmethyloxy)ethyl]-2-amino-2methylpropanamide methanesulfonate;
8) N-[1(R)-[(1,2-Dihydro-1-methanesulfonylspiro[3H-indole-3,4'-piperidin]-1'-yl)carbonyl]-2-(2',6'-difluorophenylrethyloxy)ethyl]-2-amino-2-methylpropanamide;
9) N-[1(R)-[(1,2-Dihydro-1-methanesulfonyl-5-fluorospiro[3H-indole-3,4'-piperidin]-1'-yl)carbonyl]-2-(phenylmethyloxy)ethyl]-2-amino-2-methylpropanamide;
10) N-[1(S)-[(1,2-Dihydro-1-methanesulfonylspiro[3H-indole-3,4'piperidin]-1'-yl)carbonyl]-2-(phenylmethylthio)ethyl]-2-amino-2-methylpropanamide;
11) N-[1(R)-[(1,2-Dihydro-1-methanesulfonylspiro[3H-indole-3,4'-piperidin]-1'-yl)carbonyl]-3-phenylpropyl]-2-amino-2-methylpropanamide;
12) N-[1(R)-[(1,2-Dihydro-1-methanesulfonylspiro[3H-indole-3,4'-piperidin]-1'-yl)carbonyl]-3-cyclohexylpropyl]-2-amino-2-methylpropanamide;
13) N-[1(R)-[(1,2-Dihydro-1-methanesulfonylspiro[3H-indole-3,4'-piperidin]-1'-yl)carbonyl]-4-phenylbutyl]-2-amino-2-methylpropanamide;
14) N-[1(R)-[(1,2-Dihydro-1-methanesulfonylspiro[3H-indole-3,4'-piperidin]-1'-yl)carbonyl]-2-(5-fluoro-1H-indol-3-yl)ethyl]-2-amino-2-methylpropanamide;
15) N-[1(R)-[(1,2-Dihydro-1-methanesulfonyl-5-fluorospiro[3H-indole-3,4'-piperidin]-1'-yl)carbonyl]-2-(5-fluoro-1H-indol-3-yl)ethyl]-2-amino-2-methylpropanamide;
16) N-[1(R)-[(1,2-Dihydro-1-(2-ethoxycarbonyl)methylsulfonylspiro-[3H-indole-3,4'-piperidin]-1'-yl)carbonyl]-2-(1H-indol-3-yl)ethyl]-2-amino-2-methylpropanamide;
17) N-[1(R)-[(1,2-Dihydro-1,1-dioxospiro[3H-benzothiophene-3,4'-piperidin]-1'-yl)carbonyl]-2-(phenylmethyloxy)ethyl]-2-amino-2-methylpropanamide;

and pharmaceutically acceptable salts thereof.

The compounds of the invention may also be used in combination with bisphosphonates (bisphosphonic acids) and other agents, such as growth hormone secretagogues, e.g. MK-0677, for the treatment and the prevention of disturbances of calcium, phosphate and bone metabolism, in particular, for the prevention of bone loss during therapy with the GnRH antagonist, and in combination with estrogens, progesterones and or androgens for the prevention or treatment of bone loss or hypogonadal symptoms such as hot flashes during therapy with the GnRH antagonist.

Bisphosphonates (bisphosphonic acids) are known to inhibit bone resorption and are useful for the treatment of bone lithiasis as disclosed in U.S. Pat. No. 4,621,077 to Rosini, et al.

The literature discloses a variety of bisphosphonic acids which are useful in the treatment and prevention of diseases involving bone resorption. Representative examples may be found in the following: U.S. Pat. No. 3,251,907; U.S. Pat. No. 3,422,137; U.S. Patent No. 3,584,125; U.S. Pat. No. 3,940,436; U.S. Pat. No. 3,944,599; U.S. Pat. No. 3,962,432; U.S. Pat. No. 4,054,598; U.S. Pat. No. 4,267,108; U.S. Pat. No. 4,327,039; U.S. Pat. No. 4,407,761; U.S. Pat. No. 4,578,376; U.S. Pat. No. 4,621,077; U.S. Pat. No. 4,624,947; U.S. Pat. No. 4,746,654; U.S. Pat. No. 4,761,406; U.S. Pat. No. 4,922,007; U.S. Pat. No. 4,942,157; U.S. Pat. No. 5,227,506; U.S. Pat. No. 5,270,365; EPO Patent Pub. No. 0,252,504; and *J. Org. Chem.*, 36, 3843 (1971).

The preparation of bisphosphonic acids and halo-bisphosphonic acids is well known in the art. Representative examples may be found in the above mentioned references which disclose the compounds as being useful for the treatment of disturbances of calcium or phosphate metabolism, in particular, as inhibitors of bone resorption.

Preferred bisphosphonates are selected from the group of the following compounds: alendronic acid, etidrononic acid, clodronic acid, pamidronic acid, tiludronic acid, risedronic acid, 6-amino-1-hydroxy-hexylidene-bisphosphonic acid, and 1-hydroxy-3(methylpentylamino)-propylidene-bisphosphonic acid; or any pharmaceutically acceptable salt thereof. A particularly preferred bisphosphonate is alendronic acid (alendronate), or a pharmaceutically acceptable salt thereof. An especially preferred bisphosphonate is alendronate sodium, including alendronate sodium trihydrate. Alendronate sodium has received regulatory approval for marketing in the United States under the trademark FOSAMAX®.

Additionally, a compound of the present invention may be co-administered with a 5a-reductase 2 inhibitor, such as finasteride or epristeride; a 5a-reductase 1 inhibitor such as 4,7b-dimethyl-4-aza-5a-cholestan-3-one, 3-oxo-4-aza-4,7b-dimethyl-16b-(4-chlorophenoxy)-5a-androstane, and 3-oxo-4-aza-4,7b-dimethyl-16b-(phenoxy)-5a-androstane as disclosed in WO 93/23420 and WO 95/11254; dual inhibitors of 5a-reductase 1 and 5a-reductase 2 such as 3-oxo-4-aza-17b-(2,5-trifluoromethylphenyl-carbamoyl)-5a-androstane as disclosed in WO 95/07927; antiandrogens such as flutamide, casodex and cyproterone acetate, and alpha-1 blockers such as prazosin, terazosin, doxazosin, tamsulosin, and alfuzosin.

Further, a compound of the present invention may be used in combination with growth hormone, growth hormone releasing hormone or growth hormone secretagogues, to delay puberty in growth hormone deficient children, which will allow them to continue to gain height before fusion of the epiphyses and cessation of growth at puberty.

For combination treatment with more than one active agent, where the active agents are in separate dosage formulations, the active agents may be administered separately or in conjunction. In addition, the administration of one element may be prior to, concurrent to, or subsequent to the administration of the other agent.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy beans, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of structural formula I useful in the method of the present invention range from 0.01 to 1000 mg per adult human per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four times daily.

The amount of active ingredient that may be combined with the carrier materials to produce a single dosage form will vary depending upon the host treated and the particular mode of administration.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The following examples illustrate the preparation of some of the compounds of the invention and are not to be construed as limiting the invention disclosed herein.

EXAMPLE 1.1

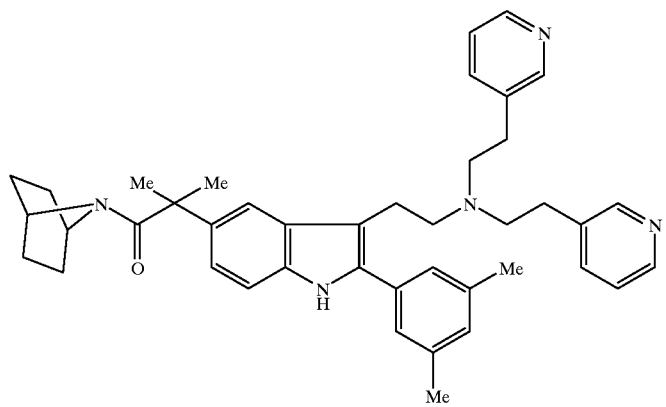

1-(7-Aza-bicyclo[2.2.1]hept-7-yl)-2-[3-{2-[bis-(2-pyridin-3-yl-ethyl)-amino]ethyl}-2-(3,5-dimethylphenyl)-1H-indol-5-yl]-2-methylpropan-1-one Step 1.1A 2-[3-(2-Aminoethyl)-2-(3,5-dimethylphenyl)-1H-indol-5-yl]-2-methlypropionic acid ethyl ester A mixture of 6.34 g (approximately 29.5 mmol) of ethyl 2-(4-hydrazinophenyl)-2-methylpropionate hydrochloride, 6.22 g (29.5 mmol) of 3-chloropropyl 3,5-dimethylphenyl ketone, and 120 mL of absolute ethanol was stirred at reflux under nitrogen for 12 hours. The cooled solution was concentrated in vacuo, and the residue was partitioned between 200 mL of ethyl acetate and 50 mL of saturated aqueous sodium carbonate solution. The organic phase was washed with 25 mL of brine, then dried over sodium sulfate, and filtered. The residue from concentration of the filtrate in vacuo was purified by flash chromatography on silica gel (elution with 95:5 $CH_2Cl_2$—MeOH and then 95:5:0.5 $CH_2Cl_2$—MeOH-concentrated $NH_{40}H$). Concentration of the product fractions gave 1.13 g (11%) of a stiff foam; nearly homogeneous by TLC in 95:5:0.5 $CH_2Cl_2$—MeOH-concentrated $NH_4OH$. 400 MHz $^1H$ NMR ($CDCl_3$) was consistent with the assigned structure.

Step 1.1B

2-[3-(2-tert-Butoxycarbonylaminoethyl)-2-(3,5-dimethylphenyl)-1H-indol-5-yl]-2-methylpropionic acid ethyl ester To a solution of 2-[3-(2-aminoethyl)-2-(3,5-dimethylphenyl)-5H-indol-5-yl]-2-methlypropionic acid ethyl ester (584 mg in 10 mL tetrahydrofuran) at 0° C. was added a solution of di-tert-butyl dicarbonate (485 mg in 2 mL tetrahydrofuran) followed by poatssium carbonate (320 mg in 4 mL water) and the resulting suspension stirred vigourously at 0° C. After 20 minutes, the reaction was quenched by the addition of excess saturated aqueous ammonium chloride and the mixture extracted with ethyl acetate. The organic portion was dried over sodium sulfate and concentrated in vacuo. The residue was purified by flash chromatography on silica gel (hexane:methylene chloride-:ethyl acetate, 7:7:1) to give the title compound (665 mg).

Step 1.1C

2-[3-(2-tert-Butoxycarbonylaminoethyl)-2-(3,5-dimethylphenyl)-1H-indol-5-yl]-2-methylpropionic acid To a stirred solution of 2-[3-(2-tert-butoxycarbonylaminoethyl)-2-(3,5-dimethylphenyl)-1H-indol-5-yl]-2-methylpropionic acid ethyl ester (665 mg in 20 mL methanol) was added 7 mL of 2.0N potassium hydroxide and the mixture heated to 94° C. on an oil bath. After 6 hours the mixture was acidified to $pH_5$ and extracted with ethyl acetate. The organic layer was washed with saturated ammonium chloride, dried over sodium sulfate and concentrated in vacuo to give the crude title compound (620 mg).

Step 1.1D

{2-[5-[2-(7-Aza-bicyclo[2.2.1]hept-7-yl)-1,1-dimethyl-2-oxo-ethyl]-2-(3,5-dimethylphenyl)-1H-indol-3-yl]-ethyl}carbamic acid tert-butyl ester To a stirred solution of 2-[3-(2-tert-butoxycarbonylaminoethyl)-2-(3,5-dimethylphenyl)-1H-indol-5-yl]-2-methylpropionic acid (247 mg in 3 mL dry methylene chloride) was added 1-hydroxybenzotriazole (111 mg) and 1-(3-dimethylaminopropyl)-3-ethylcarbodiimide hydrochloride (126 mg) and the reagents allowed to mix for 1 hour. At this time a solution of 7-aza-bicyclo[2.2.]heptane hydrochloride (130 mg in 1.5 mL methylene chloride) was added followed by 0.15 mL triehtylamine and the reaction stirred at room temperature. After 20 hours, the mixture was concentrated in vacuo and purified by flash chromatography on silica gel (hexane:ethyl acetate, 1:1) to give the title compound (252 mg).

Step 1.1E

2-[3-(2-Aminoethyl)-2-(3,5-dimethylphenyl)-1H-indol-5-yl]1-(7-aza-bicyclo[2.2.1]hept-7-yl)-2-methyl-propan-1-one To a solution of {2-[5-[2-(7-aza-bicyclo[2.2.1]hept-7-yl)-1,1-dimethyl-2-oxo-ethyl]-2-(3,5-dimethylphenyl)-1H-indol-3-yl]-ethyl} carbamic acid tert-butyl ester (252 mg in 10 mL methylene chloride) at 0° C. was added 0.60 mL anisole followed by 3.7 mL trifluoroacetic acid and the mixture stirred at 0° C. After 1.5 hours, the mixture was concentrated in vacuo and the residual acid removed by azeotrope with toluene. Purifiaction by flash chromatography on silica gel (methylene chloride:methanol:ammonium hydroxide, 90:7:1) gave the title compound (196 mg).

Step 1.1F 1-(7-Aza-bicyclo[2.2.1]hept-7-yl)-2-[3-{2-[bis-(2-pyridin-3-yl-ethyl)-amino]ethyl}-2-(3,5-dimethyl-phenyl)-1H-indol-5-yl]-2-methylpropan-1-one To a solution of pyridin-3-yl-acetaldehyde (120 mg in a mixture of 5 mL methanol and 0.018 mL glacial acetic acid) was added 141 mg of 2-[3-(2-aminoethyl)-2-(3,5-dimethylphenyl)-1H-indol-5-yl]-1-(7-aza-bicyclo[2.2.1] hept-7-yl)-2-methyl-propan-1-one followed by 20 mg 3Å powdered molecular seives. To this mixture, 68 mg sodium cyanoborohydride was added and the pH adjusted to 5.5 by the addition of 10% methanolic acetic acid. After 15.5 hours, the reaction was quenched by the addition of saturated sodium bicarbonate and the mixture extracted with ethyl acetate. The organic portion was washed successively with saturated ammonium chloride, sodium bicarbonate and brine, then dried over sodium sulfate. Purification of the concentrate by flash chromatography on silica gel (methylene chloride:methanol, 92:8) gave the title compound (130 mg). MASS: 640 (M+H)

PREPARATION OF SYNTHETIC INTERMEDIATES

Ethyl 2-(4-hydrazinophenyl)-2-methylpropionate

Step A:

Ethyl (+/−)-2-(4-nitrophenyl)propionate

To a solution of 9.76 g (50 mmol) of (+/−)-2-(4-nitrophenyl)propionic acid in 150 mL of absolute ethanol was added 3.0 mL of concentrated sulfuric acid. The resulting solution was stirred at reflux under nitrogen. After 6 hours, the solution was cooled and stirred vigorously as 250 mL of saturated aqueous sodium bicarbonate solution was added gradually (Caution: foaming). The mixture was then partitioned between 750 mL of ethyl acetate and 500 mL of water. The organic layer was washed with 100 mL of saturated aqueous sodium bicarbonate solution and then with 100 mL of saturated aqueous sodium chloride solution. The organic phase was dried over magnesium sulfate, filtered, and concentrated in vacuo to give 10.86 g (97%) of an oil; homogeneous by TLC in 9:1 hexane-ethyl acetate. 400 MHz $^1$H NMR (CDCl$_3$) was consistent with the assigned structure.

Step B:

Ethyl 2-methyl-2-(4-nitrophenyl)propionate

A suspension of 924 mg (23 mmol) of sodium hydride (60% in oil) in 21 mL of dry N,N-dimethylformamide was stirred under nitrogen in an ice bath as a solution of 4.68 g (21 mmol) of ethyl (+/−)-2-(4-nitrophenyl)propionate in 20.5 mL of dry N;N-dimethylformamide was added gradually over about 10 minutes. An intense violet color developed during the addition. The mixture was then allowed to warm to room temperature. After about 1 hour, the mixture was again cooled in an ice bath as a solution of 1.44 mL (3.28 g; 23 mmol) of methyl iodide in 5 mL of dry N,N-dimethylformamide was added dropwise by syringe over about 10 minutes, while maintaining the internal temperature at 10–15° C. The mixture was allowed to warm to room temperature, and the color changed to brown. After 1 hour, an additional 187 mL (426 mg, 3 mmol) of iodomethane was added. By the next day, the mixture consisted of a suspension of some grayish solid in a golden liquid. It was stirred vigorously and quenched by gradual addition of 10 mL of 5% aqueous potassium bisulfate solution. The mixture was partitioned between 400 mL of diethyl ether and 400 mL of water. The organic layer was washed with an additonal 3×400 mL of water and then with 50 mL of saturated aqueous sodium chloride solution. The organic phase was then dried over magnesium sulfate, filtered, and concentrated in vacuo. Flash chromatography of the residue on silica gel (elution with 19:1 hexane-ethyl acetete) yielded 4.31 g (87%) of an oil; homogeneous by TLC in 9:1 hexane-ethyl acetete. 400 MHz $^1$H NMR (CDCl$_3$) was consistent with the assigned structure.

Step C:

Ethyl 2-(4-aminophenyl)-2-methylpropionate

A mixture of 4.27 g (18 mmol) of ethyl 2-methyl-2-(4-nitrophenyl)propionate, 200 mg of 10% palladium on carbon, and 120 mL of absolute ethanol was shaken with hydrogen (initial hydrogen pressure 47 psig) in a pressure vessel for 2 hours. The catalyst was removed by filtration through Celite under nitrogen, and the filter cake was washed with additional ethanol. Concentration of the filtrate in vacuo at up to 50° C. gave 3.74 g (100%) of an oil; homogeneous by TLC in 4:1 hexane-EtOAc. 400 MHz $^1$H NMR (CDCl$_3$) was consistent with the assigned structure. Mass spectrum (ESI): m/e=208 (M+H).

Step D:

Ethyl 2-(4-hydrazinophenyl)-2-methylpropionate

A solution of 3.725 g (18 mmol) of ethyl 2-(4-aminophenyl)-2-methylpropionate in 18 mL of concentrated hydrochloric acid was stirred at −10 to −5° C. in an ice-acetone bath as a solution of 1.29 g (18.7 mmol) of sodium nitrite in 7.5 mL of water was added dropwise over about 15 minutes. Stirring was continued at this temperature for an additional 30 minutes. Next, a small amount of insoluble solid was removed by filtration into a cold receiving flask. The filtrate was then added dropwise over 10–15 minutes to a solution of 20.3 g (90 mmol) of stannous chloride dihydrate in 14.5 mL of concentrated hydrochloric acid stirred under nitrogen in an ice-acetone bath. The addition was carried out at such a rate that the internal temperature remained at about −5° C. A gummy material separated during the addition. After completion of the addition, stirring was continued at −10 to −5° C. for 1 hour. The aqueous phase was decanted, and the residual gum was dissolved in 250 mL of ethyl acetate. The ethyl acetate solution was treated cautiously with 250 mL of saturated aqueous sodium bicarbonate solution and shaken in a separatory funnel. The ethyl acetate layer was washed with 50 mL of saturated aqueous sodium chloride solution. The entire mixture was filtered before separation of the phases. The ethyl acetate phase was dried over magnesium sulfate, filtered, and concentrated in vacuo at room temperature to yield 2.59 g (65%) of an oil. 500 MHz $^1$H NMR (CDCl$_3$) was consistent with the assigned structure and indicated that only minor impurities were present.

3-Chloropropyl 3,5-dimethylphenyl ketone

Step AA:

4-Chloro-N-methoxy-N-methylbutyramide

To a solution of 4-chlorobutyryl chloride (10.0 g in 200 mL of dry methylene chloride) was added 10.4 g of N,O-dimethylhydroxylamine hydrochloride. The mixture was stirred under nitrogen and maintained below 25° C. by cooling in an ice bath as necessary while triethylamine (29.1 mL)was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1$H NMR (CDCl$_3$). Mass spectrum (PB-NH$_3$/CI): m/e=166 (M+H).

Step BB:

3–Chloropropyl 3,5-dimethylphenyl ketone

A solution of 10.2 mL (13.9 g; 72 mmol) 5-bromo-m-xylene in 200 mL of anhydrous tetrahydrofuran was stirred under nitrogen at −78° C. as 35.8 mL (84 mmol) of 2.5M n-butyllithium in tetrahydrofuran was added dropwise. After 15 minutes at −78° C., a solution of 10.0 g (60 mmol) of 4-chloro-N-methoxy-N-methylbutyramide in 30 mL of anhydrous tetrahydrofuran was added dropwise over 25–30 minutes. The resulting solution was maintained at −78° C. for 45 minutes and then warmed briefly to room temperature. The reaction was quenched by addition of 40 mL of 2N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1$H NMR (CDCl$_3$).

Pyridin-3-yl-acetaldehyde

Step AAA:

N-Methoxy-N-methyl-2-pyridin-3-yl-acetamide

To a suspension of pyridin-3-yl-acetic acid (856 mg in 20 mL dry methylene chloride) was added in sequence 0.35 mL triethylamine, 1-hydroxybenzotriazole (862 mg) and 1-(3-dimethylaminopropyl)-3-ethylcarbodiimide hydrochloride (1.08 g) and the reagents allowed to mix for 1 hour. At this time, N,O-dimethylhydroxylamine hydrochloride (1.22 g) was added followed by 2.0 mL triethylamine and the reaction stirred at room temperature. After 20 hours, the mixture applied to a silica gel column and purified by flash chromatography (methylene chloride:methanol, 94:6) to give the title compound (796 mg).

Step BBB:

Pyridin-3-yl-acetaldehyde

To a solution of N-methoxy-N-methyl-2-pyridin-3-yl-acetamide (279 mg in 5 mL dry tetrahydrofuran) at −30° C. was added 3.1 mL of a 1M diisobutylaluminum hydride solution in tetrahydrofuran and the mixture stirred at low temperature. After 30 minutes, the reaction was quenched by the careful addition of saturated aqueous sodium potassium tartarate. The resulting mixture was allowed to stir while warming to room temperature at which time the mixture was diluted with ethyl acetate and filtered through a pad of sodium sulfate. Purification of the concentrate by flash chromatography on silica gel (methylene chloride:methanol, 94:6) gave the title compound (120 mg).

EXAMPLE 1.2

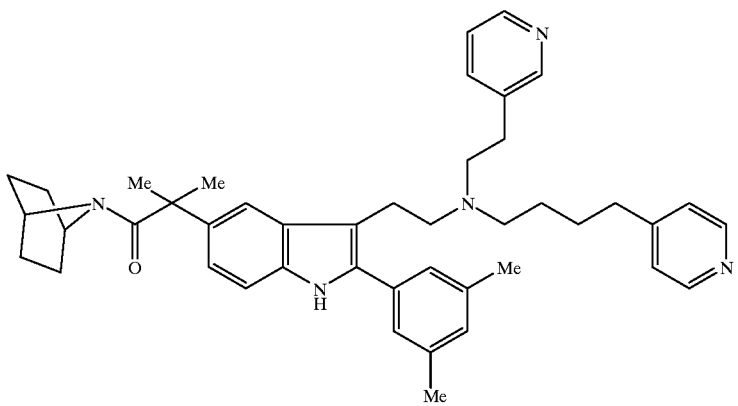

1-(7-Aza-bicyclo[2.2.1]hept-7-yl)-2-(2-(3,5-dimethylphenyl)-3-{2-[(4-pyridin-4-yl-butyl)-
(2-pyridin-3-yl-ethyl)amino]ethyl}-1H-indol-5-yl)-2-methylpropan-1-one

Step 1.2A 1-(7-Aza-bicyclo[2.2.1]hept-7-yl)-2-{2-(3,5-dimethylphenyl)-3-[2-(2-pyridin-3-yl-ethylamino)-ethyl]-1H-indol-5-yl}-2-methylpropan-1-one To a solution of 2-[3-(2-aminoethyl)-2-(3,5-dimethylphenyl)-1H-indol-5-yl]-1-(7-aza-bicyclo[2.2.1]hept-7-yl)-2-methylpropan-1-one (183 mg in 10 mL dry chloroform) at 0° C. was added 305 mg magnesium sulfate followed by a solution of 100 mg pyridin-3-yl-acetaldehyde in 1.0 mL chloroform and the mixture stirred at low temperature. After 6 minutes, a solution of 52 mg sodium cyanoborohydride in 0.80 mL methanol was added and the pH djusted to pH$_6$ by the addition of 10% acetic acid in methanol. After 30 minutes, the reaction was quenched by the addition of saturated sodium bicarbonate and the mixture extracted with ethyl acetate. The organic portion was washed successively with saturated ammonium chloride, sodium bicarbonate and brine, then dried over sodium sulfate. Purification of the concentrate by flash chromatography on silica gel (methylene chloride:methanol, 93:7; then 88:12) gave the title compound (118 mg).

Step 1.2B 1-(7-Aza-bicyclo[2.2.1]hept-7-yl)-2-(2-(3,5-dimethylphenyl)-3-{2-[(4-pyridin-4-yl-butyl)-(2-pyridin-3-yl-ethyl)amino]ethyl}-1H-indol-5-yl)-2-methylpropan-1-one To a solution of 4-(pyridin-4-yl)butyraldehyde (29 mg in 1.5 mL dry methanol) was added 18 mg of 1-(7-aza-bicyclo[2.2.1]hept-7-yl)-2-(2-(3,5-dimethylphenyl)-3-[2-(2-pyridin-3-yl-ethylamino)-ethyl]-1H-indol-5-yl}-2-methylpropan-1-one followed by 10 mg 3A powdered molecular seives. To this mixture, 13 mg sodium cyanoborohydride was added and the pH adjusted to 5.5 by the addition of 10% methanolic acetic acid. After 17.5 hours, the reaction was quenched by the addition of saturated sodium bicarbonate and the mixture extracted with ethyl acetate. The organic portion was washed successively with saturated ammonium chloride, sodium bicarbonate and brine, then dried over sodium sulfate. Purification of the concentrate by flash chromatography on silica gel (methylene chloride:methanol, 90:10) gave the title compound (17 mg).

PREPARATION OF SYNTHETIC INTERMEDIATES 4-(Pyridin-4-yl)butyraldehyde

Step A:

4-(4-Pyridyl)-3-pentyn-1-ol

4-Bromopyridine hydrochloride salt (5.5 g) was dissolved in a solvent mixture comprising triethylamine (50 mL) and water (10 mL). Anhydrous lithium chloride (100 mg), cooper (I) bromide powder (100 mg) and but-3-yn-1-ol (2.17 g) was added to the pyridine salt and the mixture stirred as an active nitrogen gas stream passed gently through the solution for approximately 15 minutes after which time tetrakis (triphenylphosphine)palladium (250 mg) was added. The reaction mixture was heated to reflux under a nitrogen atmosphere and maintained at reflux for 2.5 h after which heating was stopped and the reaction allowed to cool to room temperature. The mixture was concentrated in vacuo and the residue treated with 3M sodium hydroxide, extracted with chloroform and concentrated in vacuo. Purification of the residue by flash chromatography on silica gel (ethyl acetate) gave the title compound (3.74 g).

Step B:

4-(4-Pyridyl)-butan-1-ol 4-(4-Pyridyl)-3-butyn-1-ol (3.5 g) was dissolved in methanol (100 mL) in a Parr hydrogenation bottle and platinum (IV) oxide [Adams' Catalyst] (0.3 g) was added. The Parr bottle was placed on a Parr hydrogenation apparatus and the solution hydrogenated at 40 psi for 2.5 h after which time the starting material had been judged to be consumed by TLC. The spent catalyst was removed by filtration through a Celite pad and the pad carefully washed with more methanol. The combined filtrates were evaporated under reduced pressure on a rotary evaporator and the oily residues then subjected to column chromatography on a short silica column using neat ethyl acetate as the eluant to provide the title compound (3.0 g).

Step C:

4-(Pyridin-4-yl)butyraldehyde

Oxalyl chloride (1.45 mL of a 2M solution in dry methylene chloride) was placed in an oven-dried flask and cooled to −78° C. using a dry ice and acetone cooling bath and a solution of DMSO (0.413 mL) in dry methylene chloride (1 mL) added drop by drop to the oxalyl chloride over 3 minutes and stirred for a further 3 minutes. A solution of 4-(4-pyridyl)-butan-1-ol (400 mg) in dry methylene chloride (5 mL) was added to the reaction flask over approx. 3 minutes and the reaction stirred for 15 minutes. Anhydrous triethylamine (2.03 mL) was added and the reaction mixture stirred for another 2 hours during which time the cold bath had warmed up to room temperature. The reaction was quenched by the addition of saturated brine and then partitioned with methylene chloride. The aqueous layer was discarded and the methylene chloride extract dried over anhydrous sodium sulfate powder, filtered and evaporated under reduced pressure to leave an oily residue. The product was isolated by column chromatography on silica gel using ethyl acetate as eluant (301 mg).

Following a procedure similar to that described in EXAMPLE 1, the following compounds were prepared:

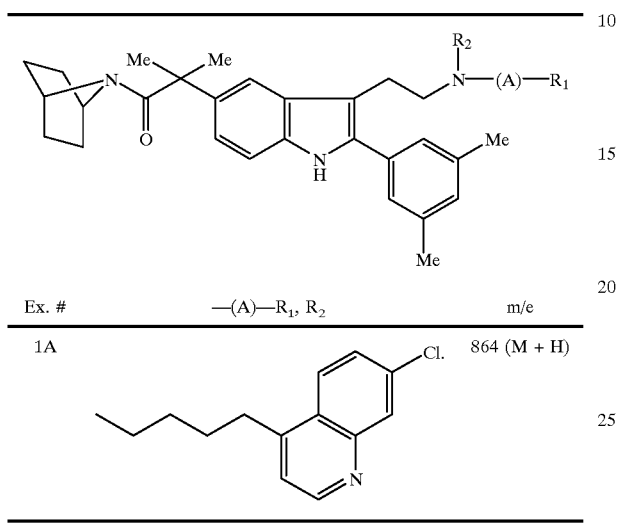

| Ex. # | —(A)—$R_1$, $R_2$ | m/e |
|---|---|---|
| 1A | (4-pentylquinolin-7-yl chloride) | 864 (M + H) |

EXAMPLE 2

Following a procedure similar to that described in EXAMPLE 1, the following compounds were prepared:

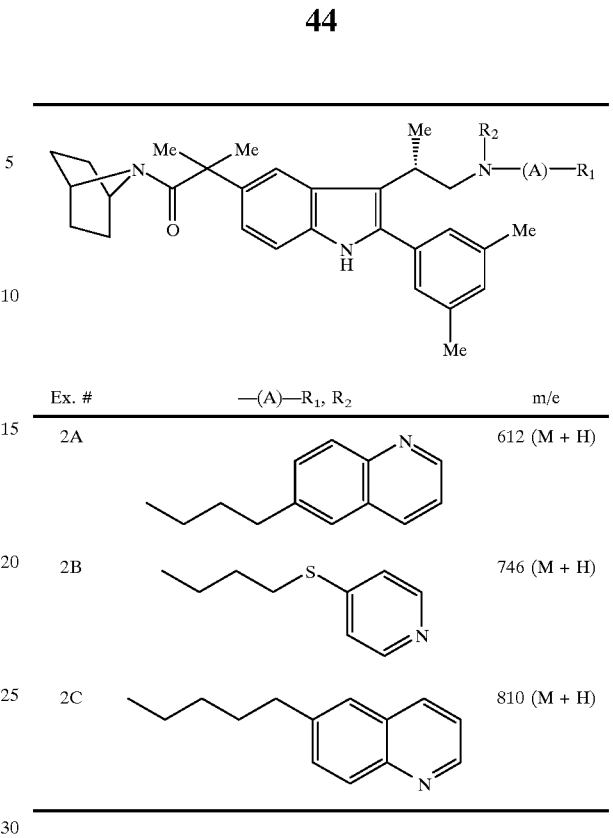

| Ex. # | —(A)—$R_1$, $R_2$ | m/e |
|---|---|---|
| 2A | (butyl quinoline) | 612 (M + H) |
| 2B | (butyl thiopyridine) | 746 (M + H) |
| 2C | (pentyl quinoline) | 810 (M + H) |

EXAMPLE 3

Following a procedure similar to that described in EXAMPLE 1, the following compounds were prepared:

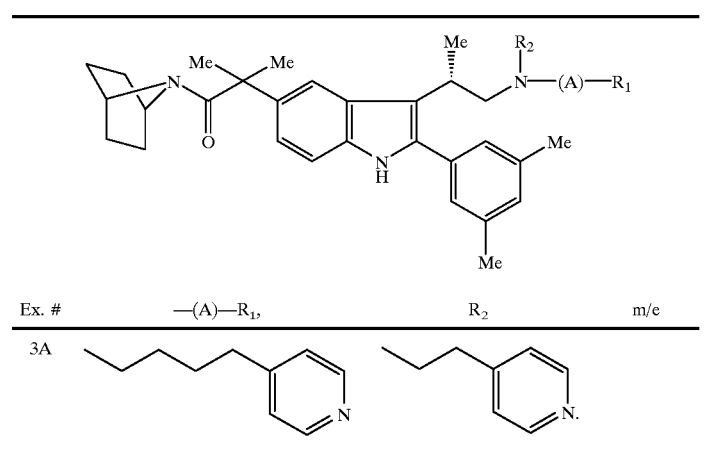

| Ex. # | —(A)—$R_1$, | $R_2$ | m/e |
|---|---|---|---|
| 3A | (butylpyridine) | (ethylpyridine) | |

EXAMPLE 4

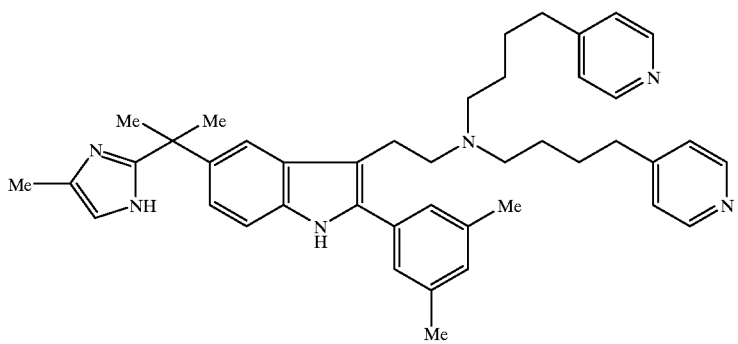

(2-{2-(3,5-Dimethylphenyl)-5-[1-methyl-1-(4-methyl-1H-imidazol-2-yl)-ethyl]-1H-indol-3-yl}ethyl bis-(4-pyridin-4-yl-butyl)-amine

Step 4A

2-[3-(2-tert-Butoxycarbonylaminoethyl)-2-(3,5-dimethylphenyl)-1H-indol-5-yl]-2-methyl-propionic acid ethyl ester To a solution of 2-[3-(2-aminoethyl)-2-(3,5-dimethylphenyl)-1H-indol-5-yl]-2-methylpropionic acid ethyl ester (1.13 g in 20 mL methylene chloride) at 0° C. was added triethylamine (0.84 mL) and a solution of 982 mg di-tert-butyl dicarbonate in 5 mL methylene chloride and the resulting solution stirred vigourously at 0° C. After 2 hours, the reaction was quenched by the addition of excess saturated aqueous sodium bicarbonate and the mixture extracted with methylene chloride. The organic portion was dried over sodium sulfate and concentrated in vacuo. The residue was purified by flash chromatography on silica gel (hexane:ethyl acetate, 85:15) to give the title compound (1.28 g).

Step 4B

2-[3-(2-tert-Butoxycarbonylamino-ethyl)-2-(3,5-dimethylphenyl)-1H-indol-5-yl]-2-methylpropionic acid To a stirred solution of 2-[3-(2-tert-butoxycarbonylaminoethyl)-2-(3,5-dimethylphenyl)-1H-indol-5-yl]-2-methyl-propionic acid ethyl ester (1.28 g in 25 mL ethanol) was added 30 mL of 0.5N sodium hydroxide and the mixture heated to 90° C. on an oil bath. After 30 hours the mixture was concentrated in vacuo, diluted with water and extracted with diethyl ether (3×). The aqueous layer was then made acidic by the addition of 0.5N hydrochloric acid and extracted with ethyl acetate. The ethyl acetate layer was washed with water and brine, dried over sodium sulfate and concentrated in vacuo to give the crude title compound (1.23 g).

Step 4C (2-{2-(3,5-Dimethylphenyl)-5-[1-(methoxymethylcarbamoyl)-1-methyl-ethyl]-1H-indol-3-yl}ethyl)carbamic acid tert-butyl ester To a suspension of 2-[3-(2-tert-butoxycarbonylaminoethyl)-2-(3,5-dimethylphenyl)-1H-indol-5-yl]-2-methylpropionic acid (1.23 g in 15 mL N,N-dimethylformamide) at 0° C. was added 608 mg of 1-hydroxybenzotriazole (HOBt), 0.48 mL 4-methylmorpholine and 352 mg of N,O-dimethylhydroxylamine hydrochlorideand the mixture stirred at low temperature. After 15 minutes, 826 mg 1-(3-dimethylaminopropyl)-3-ethylcarbodiimide hydrochloride (EDC) were added and the mixture warmed to room temperature. The reaction was quenched after 3.5 days by concentration in vacuo, resuspending in ethyl acetate and washing sequentially with water, 0.3N sodium bisulfate, water, saturated sodium bicarbonate and brine. The organic portion was dried over sodium sulfate and the concentrate purified by flash chromatography on silica gel (hexane:ethyl acetate, 3:1) to give the title compound (905 mg).

Step 4D

{2-[5-(1,1-Dimethyl-2-oxo-ethyl)-2-(3,5-dimethylphenyl)-1H-indol-3-yl]ethyl}carbamic acid tert-butyl ester To a solution of (2-{2-(3,5-dimethylphenyl)-5-[1-(methoxymethylcarbamoyl)-1-methyl-ethyl]-1H-indol-3-yl}ethyl)carbamic acid tert-butyl ester (296 mg in 5 mL dry tetrahydrofuran) at 0° C. was added 1.8 mL of a 1M lithium aluminum hydride solution in tetrahydrofuran and the mixture stirred at low temperature. After 1 hour, the reaction was quenched by the careful addition of 0.3M aqueous sodium bisulfate solution. The resulting mixture was extracted with ethyl acetate and the organic portion washed successively with 0.3M aqueous sodium bisulfate, water and brine. This was then dried over sodium sulfate, concentrated in vacuo and purified by flash chromatography on silica gel (hexane:ethyl acetate, 85:15) to give the title compound (253 mg).

Step 4E (2-{2-(3,5-Dimethylphenyl)-5-[1-methyl-1-(4-methyl-1H-imidazol-2-yl)ethyl]-1H-indol-3-yl}ethyl)carbamic acid tert-butyl ester To a solution of {2-[5-(1,1-dimethyl-2-oxo-ethyl)-2-(3,5-dimethylphenyl)-1H-indol-3-yl]ethyl}carbamic acid tert-butyl ester (475 mg in 15 mL methanol) was added 1 mL of a 40% aqueous solution of pyruvic aldehyde followed by 2.2 mL ammonium hydroxide and the mixture stirred at room temperature. After 2 days, an additional portion of 40% aqueous pyruvic aldehyde (0.50 mL) and ammonium hydroxide (1.1 mL) were added. Finally after 4 days the reaction mixture was concentrated in vacuo, the residue resolvated in ethyl acetate and washed sequentially with water and brine. The combined organics were dried over sodium sulfate and the concentrate purified by flash chromatography on silica gel (hexane:ethyl acetate, 1:4) to give the title compound (402 mg).

Step 4F

2-{2-(3,5-Dimethylphenyl)-5-[1-methyl-1-(4-methyl-1H-imidazol-2-yl)ethyl]-1H-indol-3-yl}ethylamine To a solution of (2-{2-(3,5-dimethylphenyl)-5-[1-methyl-1-(4-methyl-1H-imidazol-2-yl)ethyl]-1H-indol-3-yl}ethyl) carbamic acid tert-butyl ester (353 mg in 8 mL methylene chloride) at 0° C. was added 0.56 mL anisole followed by 2.5 mL trifluoroacetic acid and the mixture stirred at room temperature. After 2 hours, the mixture was concentrated in vacuo and the residual acid removed by azeotrope with toluene. The residue was solvated in methylene chloride and washed sequentially with 0.5N sodium hydroxide and brine. Purification of the concentrate by preparative tlc on silica gel (methylene chloride:methanol:ammonium hydroxide, 80:20:0.25) to give the title compound (198 mg).

Step 4G (2-{2-(3,5-Dimethylphenyl)-5-[1-methyl-1-(4-methyl-1H-imidazol-2-yl)-ethyl]-1H-indol-3-yl}ethyl)bis-(4-pyridin-4-yl-butyl)-amine A mixture of 2-{2-(3,5-dimethylphenyl)-5-[1-methyl-1-(4-methyl-1H-imidazol-2-yl)ethyl]-1H-indol-3-yl}ethylamine (97 mg) and 4-pyridin-4-yl butyraldehyde (41 mg) were solvated in 5 mL dry methanol to which ca. 0.75 g powdered 3 Å molecular sieves were added. The pH of this mixture was adjusted to 5 by the addition of acetic acid and then 1.0 mL of a 1M solution of sodium cyanoborohydride in tetrahydrofuran was added and the mixture atirred at room temperature. After 22 hours, the mixture was filtered through diatomaceous earth, concentrated in vacuo and purified by flash chromatography on silica gel (methylene chloride: methanol:ammonium hydroxide, 80:20:0.25) to give the title compound (39 mg). MASS: 653 (M+H)

PREPARATION OF SYNTHETIC INTERMEDIATES 4-(Pyridin-4-yl)butyraldehyde

Step A:

4-(4-Pyridyl)-3-pentyn-1-ol

4-Bromopyridine hydrochloride salt (5.5 g) was dissolved in a solvent mixture comprising triethylamine (50 mL) and water (10 mL). Anhydrous lithium chloride (100 mg), cooper (I) bromide powder (100 mg) and but-3-yn-1-ol (2.17 g) was added to the pyridine salt and the mixture stirred as an active nitrogen gas stream passed gently through the solution for approximately 15 minutes after which time tetrakis (triphenylphosphine)palladium (250 mg) was added. The reaction mixture was heated to reflux under a nitrogen atmosphere and maintained at reflux for 2.5h after which heating was stopped and the reaction allowed to cool to room temperature. The mixture was concentrated in vacuo and the residue treated with 3M sodium hydroxide, extracted with chloroform and concentrated in vacuo. Purification of the residue by flash chromatography on silica gel (ethyl acetate) gave the title compound (3.74 g).

Step B:

4-(4-Pyridyl)-butan-1-ol 4-(4-Pyridyl)-3-butyn-1-ol (3.5 g) was dissolved in methanol (100 mL) in a Parr hydrogenation bottle and platinum (IV) oxide [Adams' Catalyst] (0.3 g) was added. The Parr bottle was placed on a Parr hydrogenation apparatus and the solution hydrogenated at 40 psi for 2.5 h after which time the starting material had been judged to be consumed by TLC. The spent catalyst was removed by filtration through a Celite pad and the pad carefully washed with more methanol. The combined filtrates were evaporated under reduced pressure on a rotary evaporator and the oily residues then subjected to column chromatography on a short silica column using neat ethyl acetate as the eluant to provide the title compound (3.0 g).

Step C:

4-(Pyridin-4-yl)butyraldehyde

Oxalyl chloride (1.45 mL of a 2M solution in dry methylene chloride) was placed in an oven-dried flask and cooled to −78° C. using a dry ice and acetone cooling bath and a solution of DMSO (0.413 mL) in dry methylene chloride (1 mL) added drop by drop to the oxalyl chloride over 3 minutes and stirred for a further 3 minutes. A solution of 4-(4-pyridyl)-butan-1-ol (400 mg) in dry methylene chloride (5 mL) was added to the reaction flask over approx. 3 minutes and the reaction stirred for 15 minutes. Anhydrous triethylamine (2.03 mL) was added and the reaction mixture stirred for another 2 hours during which time the cold bath had warmed up to room temperature. The reaction was quenched by the addition of saturated brine and then partitioned with methylene chloride. The aqueous layer was discarded and the methylene chloride extract dried over anhydrous sodium sulfate powder, filtered and evaporated under reduced pressure to leave an oily residue. The product was isolated by column chromatography on silica gel using ethyl acetate as eluant (301 mg).

Following a procedure similar to that described in EXAMPLE 4, the following compounds were prepared:

| Ex. # | X-R₇, R₈ | —(A)—R₁, R₂ | m/e |
|---|---|---|---|
| 4A | imidazole with C(Me)₂ | pentyl-4-pyridyl | 506 (M + H) |
| 4B | methylimidazole with C(Me)₂ | pentyl-3-pyridyl | 520 (M + H) |
| 4C | 2-methyl-imidazole, Me | pentyl-4-pyridyl | 478 (M + H) |

EXAMPLE 5

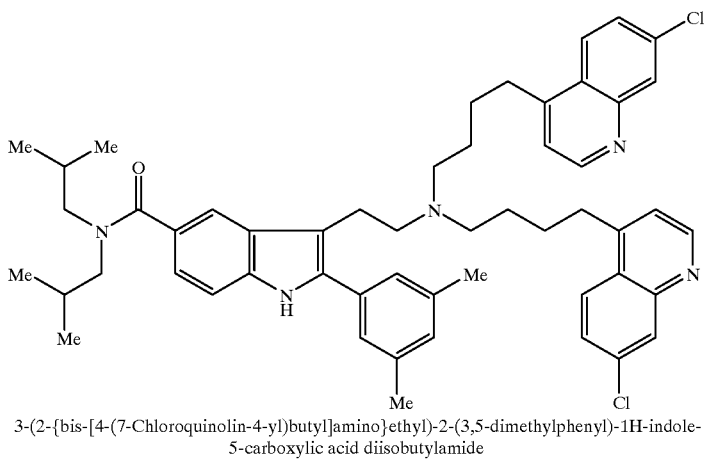

3-(2-{bis-[4-(7-Chloroquinolin-4-yl)butyl]amino}ethyl)-2-(3,5-dimethylphenyl)-1H-indole-5-carboxylic acid diisobutylamide

Step 6A

3-(2-Aminoethyl)-2-(3,5-dimethylphenyl)-1H-indole-5-carboxylic acid ethyl ester A mixture of 7.60 g (50 mmol) of 4-hydrazinobenzoic acid, 10.55 g (50 mmol) of 3-chloropropyl 3,5-dimethylphenyl ketone, and 200 mL of absolute ethanol was stirred under nitrogen and heated to reflux. After 12 hours, the mixture was cooled and filtered. The solid on the filter was washed with additional small volumes of ethanol. The filtrate was treated with 4 mL of concentrated sulfuric acid and stirred at reflux under nitrogen for 4 days. The cooled mixture was stirred in an ice bath as a solution of sodium ethoxide (21% w/w in ethanol) was added drop-wise until the mixture was basic by pH paper. The mixture was filtered and concentrated in vacuo at 30° C. The residue was partitioned between diethyl ether and water, with some saturated aqueous sodium chloride solution added to assist in separation of the layers. The aqueous phase was washed with an additional 100 mL of ether. The combined organic extracts were dried over sodium sulfate, filtered, and concentrated in vacuo. The residual gum was purified by flash chromatograpy on silica gel (elution with 97:3:0.3 and then 95:5:0.5 methylene chloride:methanol:ammonium hydroxide) to give the title compound (4.8 g). 400 MHz ¹H NMR (CDCl₃) was consistent with the assigned structure. Mass spectrum (PB-NH₃/CI): m/e=337 (M+H).

Step 5B 3-(2-tert-Butoxycarbonylamino-ethyl)-2-(3,5-dimethylphenyl)-1H-indole-5-carboxylic acid ethyl ester To a solution of 3-(2-aminoethyl)-2-(3,5-dimethylphenyl)-1H-indole-5-carboxylic acid ethyl ester (1.5 g in 30 mL dry tetrahydrofuran) at 0° C. was added a solution of di-tert-butyl dicarbonate (1.9 g in 3 mL tetrahydrofuran) followed by an aqueous solution of potassium carbonate (1 g in 10 mL water) and the resulting suspension stirred vigourously at 0° C. After 12 minutes, the reaction was quenched by the addition of excess saturated aqueous ammonium chloride and the mixture extracted with ethyl acetate. The organic portion was dried over sodium sulfate and concentrated in vacuo. The resulting solid was washed sequentially with methylene chloride, hexane and ethyl acetate to give the title compound (1.77 g).

Step 5C

3–2-tert-Butoxycarbonylaminoethyl)-2-(3,5-dimethylphenyl)-1H-indole-5-carboxylic acid To a suspension of 3-(2-tert-butoxycarbonylamino-ethyl)-2-(3,5-dimethylphenyl)-1H-indole-5-carboxylic acid ethyl ester (830 mg in 50 mL methanol) was added 8 mL of a 1.25N sodium hydroxide solution and the mixture heated to 75° C. on an oil bath. After 5.5 hours, an additional 3 mL of 1.25N sodium hydroxide were added and the reaction allowed to proceed for 2 more hours. At this time the mixture was cooled to room temperature and the reaction quenched by the addition of pH$_2$ buffer. The mixture was extracted with the ethyl acetate, washed with saturated ammonium chloride solution and the organic portion dried over sodium sulfate. Concentration in vacuo provided the crude acid in quantitative yield.

Step 5D

{2-[5-Diisobutylcarbamoyl-2-(3,5-dimethylphenyl)-1H-indol-3-yl]ethyl}carbamic acid tert-butyl ester To a solution of 3-(2-tert-butoxycarbonylaminoethyl)-2-(3,5-dimethylphenyl)-1H-indole-5-carboxylic acid (200 mg in 12 mL methylene chloride) was added 104 mg 1-hydroxybenzotriazole followed by 118 mg 1-(3-dimethylaminopropyl)-3-ethylcarbodiimide hydrochloride and the mixture stirred at room temperature. After 30 minutes, 0.35 mL of diisobutylamine was added and the mixture stirred at room temperature for 14 hours. The reaction was then concentrated in vacuo and purified by flash chromatography on silica gel (hexane:ethyl acetate, 2:1) to give the title compound (230 mg).

Step 5E 3-(2-Aminoethyl)-2-(3,5-dimethylphenyl)-1H-indole-5-carboxylic acid diisobutylamide To a solution of {2-[5-diisobutylcarbamoyl-2-(3,5-dimethylphenyl)-1H-indol-3-yl]-ethyl}carbamic acid tert-butyl ester (230 mg in 12 mL methylene chloride) at 0° C. was added 0.55 mL anisole followed by 3.4 mL trifluoroacetic acid and the mixture stirred at 0° C. After 1 hour, the mixture was concentrated in vacuo and the residual acid removed by azeotrope with toluene. Purification of the concentrate by flash chromatography on silica gel (methylene chloride:methanol:ammonium hydroxide, 90:8:1) gave the title compound (173 mg).

Step 5F 3-(2-{Bis-[4-(7-chloroquinolin-4-yl)butyl] amino}ethyl)-2-(3,5-dimethylphenyl)-1H-indole-5-carboxylic acid diisobutylamide To a solution of 3-(2-aminoethyl)-2-(3,5-dimethylphenyl)-1H-indole-5-carboxylic acid diisobutylamide (89 mg in 3.0 mL dry tetrahydrofuran) at 0° C. was added 50 mg 4-(7-chloroquinolin-4-yl)butyraldehyde and the mixture stirred for 10 minutes. At this time, 67.4 mg sodium triacetoxyborohydride were added and the mixture allowed to warm slowly to room temperature. After 5 hours, the reaction was quenched by the addition of brine and the mixture extracted with methylene chloride. The combined organics were dried over sodium sulfate and the concentrate purified by preparative tlc on silica gel (methylene chloride:methanol, 95:5) to give the title compound (21.8 mg).

PREPARATION OF SYNTHETIC INTERMEDIATES 4-(7-Chloroquinolin-4-yl)butyraldehyde

Step A 4-(7-Chloroquinolin-4-yl)butyn-1-ol

To a solution of 4,7-dichloroquinoline (3.96 g in 85 mL N,N-dimethylformamide) was added 3.16 g of 3-butyn-1-ol followed by 15 mL triethylamine and the mixture de-oxygenated with a stream of nitrogen. To this, 1.15 g tetrakis(triphenylphosphine)palladium was added followed by 143 mg copper(I) bromide and 848 mg lithium chloride and the mixture heated to reflux on an oil bath. After 4 hours, the mixture was cooled to room temperature and concentrated in vacuo. Purification od the residue by flash chromatography on silica gel (ethyl acetate:hexane, 2:1; then ethylk acetate) gave the title compound (2.3 g).

Step B 4-(7-Chloroquinolin-4-yl)butan-1-ol 4-(7-chloroquinolin-4-yl)butyn-1-ol (1 g) was dissolved in ethanol (25 mL) in a Parr hydrogenation bottle and platinum (IV) oxide [Adams' Catalyst] (100 mg) was added. The Parr bottle was placed on a Parr hydrogenation apparatus and the solution hydrogenated at 50 psi for 2 hours after which time the starting material had been judged to be consumed by TLC. The spent catalyst was removed by filtration through a Celite pad and the pad carefully washed with more ethanol. The combined filtrates were evaporated in vacuo and the residue purified by flash chromatography on silica gel (ethyl acetate; then ethyl acetate:methanol, 95:5) to give the title compound (500 mg).

Step C 4-(7–Chloroquinolin-4-yl)butyraldehyde

Oxalyl chloride (0.42 mL of a 2M solution in dry methylene chloride) was placed in an oven-dried flask, cooled to −78° C. and a solution of 99 mg methylsulfoxide in dry methylene chloride (2 mL) added drop by drop to the oxalyl chloride over 3 minutes and stirred for a further 3 minutes. A solution of 4-(7-chloroquinolin-4-yl)butan-1-ol (100 mg) in dry methylene chloride (1 mL) was added to the reaction flask over approx. 3 minutes followed by anhydrous triethylamine (0.42 mL) and the reaction mixture stirred for another 2.5 hours during which time it was allowed warmed up to room temperature. The reaction was quenched by the addition of saturated brine and then partitioned with methylene chloride. The aqueous layer was discarded and the methylene chloride extract dried over anhydrous sodium sulfate powder, filtered and concentrated in vacuo. The title compound was isolated by flash chromatography on silica gel (ethyl acetate:hexane, 2:1; then ethyl acetate), 57 mg.

3-Chloropropyl 3,5-dimethylphenyl ketone

Step AA:

4-Chloro-N-methoxy-N-methylbutyramide

To a solution of 4-chlorobutyryl chloride (10.0 g in 200 mL of dry methylene chloride) was added 10.4 g of N,O-dimethylhydroxylamine hydrochloride. The mixture was stirred under nitrogen and maintained below 25° C. by cooling in an ice bath as necessary while triethylamine 5 (29.1 mL) was added dropwise over about 20 minutes, resulting in precipitation. After 1.5 hours at room temperature, the mixture was concentrated in vacuo. The residue was partitioned between 100 mL of diethyl ether and 100 mL of saturated aqueous sodium bicarbonate solution. The organic layer was washed with an additional 100 mL of saturated sodium bicarbonate, and the aqueous fractions were back-extracted with ether. The combined organic phases were dried over sodium sulfate, filtered, and concentrated in vacuo to give 10.5 g (90%) of an oil, which had satisfactory purity by $^1$H NMR (CDCl$_3$). Mass spectrum (PB-NH$_3$/CI): m/e=166 (M+H).

Step BB:

3-Chloropropyl 3,5-dimethylphenyl ketone

A solution of 10.2 mL (13.9 g; 72 mmol) 5-bromo-m-xylene in 200 mL of anhydrous tetrahydrofuran was stirred under nitrogen at −78° C. as 35.8 mL (84 mmol) of 2.5M n-butyllithium in tetrahydrofuran was added dropwise. After 15 minutes at −78° C., a solution of 10.0 g (60 mmol) of 4-chloro-N-methoxy-N-methylbutyramide in 30 mL of anhydrous tetrahydrofuran was added dropwise over 25–30 minutes. The resulting solution was maintained at −78° C. for 45 minutes and then warmed briefly to room temperature. The reaction was quenched by addition of 40 mL of 2N hydrochloric acid and then partitioned between ethyl acetate and water. The organic phase was washed with saturated aqueous sodium bicarbonate solution and then saturated aqueous sodium chloride solution. The organic solution was dried over sodium sulfate, filtered, and concentrated in vacuo. Flash chromatography of the residue afforded 8.91 g (70%) of an oil, which had satisfactory purity by $^1$H NMR (CDCl$_3$).

Following a procedure similar to that described in EXAMPLE 5, the following compounds were prepared:

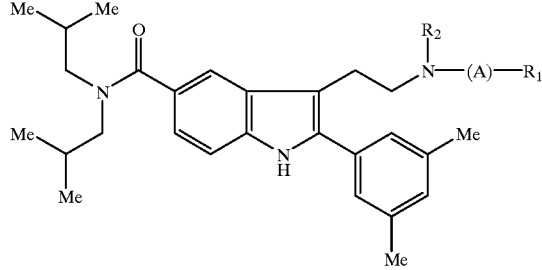

| Example # | —(A)—R$_1$, R$_2$ | m/e |
|---|---|---|
| 5A | 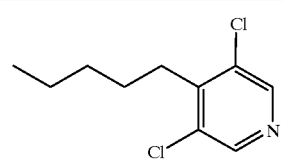 | |
| 5B | 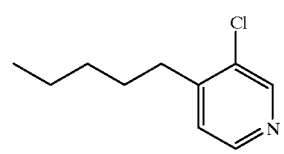 | |

What is claimed is:

1. A compound of the formula

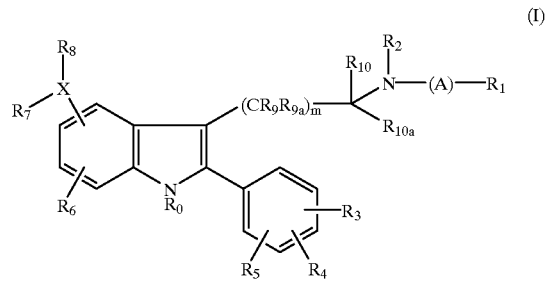
(I)

wherein

A is C$_1$–C$_6$ alkyl, substituted C$_1$–C$_6$ alkyl, C$_3$–C$_7$ cycloalkyl, substituted C$_3$–C$_7$ cycloalkyl, C$_3$–C$_6$ alkenyl, substituted C$_3$–C$_6$ alkenyl, C$_3$–C$_6$ alkynyl, substituted C$_3$–C$_6$ alkynyl, C$_1$–C$_6$ alkoxy, or C$_0$–C$_5$ alkyl-S(O)$_n$-C$_0$–C$_5$ alkyl, C$_0$–C$_5$ alkyl-O-C$_0$–C$_5$ alkyl, C$_0$–C$_5$ alkyl-NR$_{18}$—C$_0$–C$_5$ alkyl where R$_{18}$ and the C$_0$–C$_5$ alkyl can be joined to form a ring,

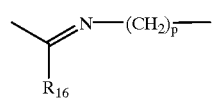

or a single bond;

R$_0$ is hydrogen, C$_1$–C$_6$ alkyl, substituted C$_1$–C$_6$ alkyl, wherein the substituents are as defined below; aryl, substituted aryl, aralkyl or substituted aralkyl, wherein the substituents are as defined for R$_3$, R$_4$ and R$_5$;

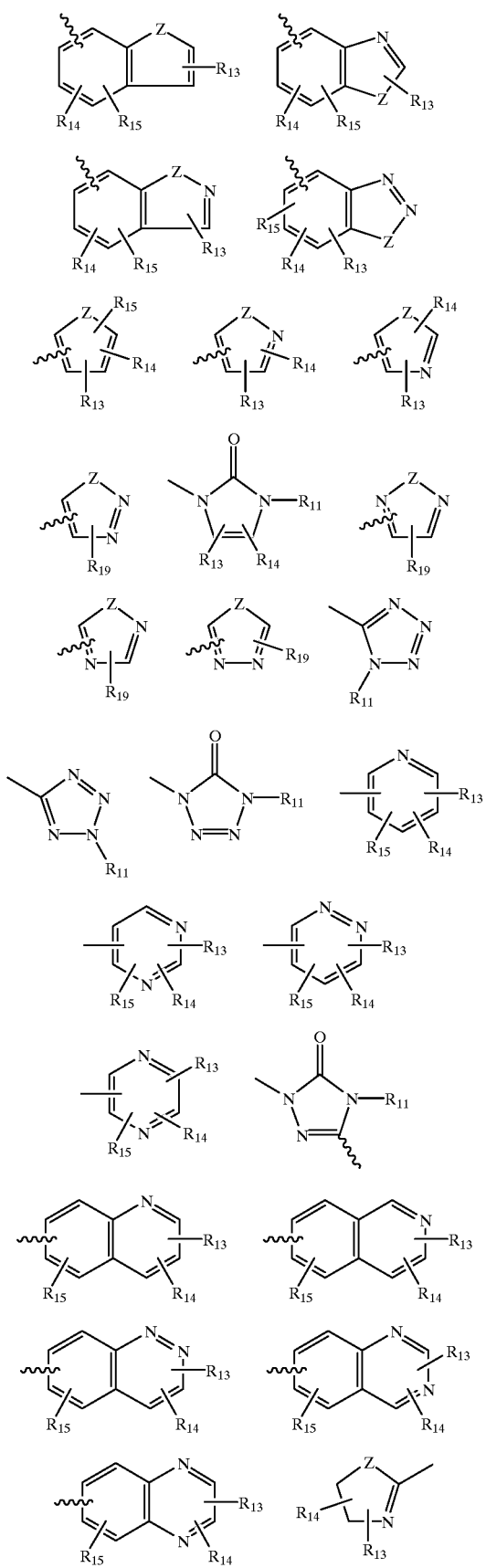

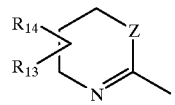

the nitrogen atoms contained in the $R_1$ heteroaromatic rings may exist either as drawn or, when chemically allowed, in their oxidized (N→O) state;

$R_2$ is heteroaryl, substituted heteroaryl, $C_1$–$C_6$ heteroaralkyl, $C_1$–$C_6$ substituted heteroaralkyl;

$R_3$, $R_4$ and $R_5$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{11}O(CH_2)_p$—, —$CH_2)_pS(O)_nR_{17}$ or halogen; wherein $R_{17}$ is hydrogen, $C_1$–$C_6$ alkyl, $C_1$–$C_3$ perfluoroalkyl, aryl or substituted aryl; or $R_3$ and $R_4$ taken together form a carbocyclic ring of 3–7 carbon atoms or a heterocyclic ring containing 1–3 heteroatoms selected from N, O and S;

$R_6$ is hydrogen, $C_1$–$C_6$ alkyl, substituted $C_1$–$C_6$ alkyl, aryl, substituted aryl, $C_1$–$C_3$ perfluoroalkyl, CN, $NO_2$, halogen, $R_{16}O(CH_2)_p$—;

$R_7$ is hydrogen, $C_1$–$C_6$ alkyl, or substituted $C_1$–$C_6$ alkyl, unless X is hydrogen or halogen, then $R_7$ is absent;

$R_8$ is hydrogen, $C(O)OR_9$, $C(O)NR_{11}R_{12}$, $NR_{11}R_{12}$, $C(O)R_{11}$, $NR_{12}C(O)R_{11}$, $NR_{12}C(O)NR_{11}R_{12}$, $NR_{12}S(O)_2R_{11}$, $NR_{12}S(O)_2NR_{11}R_{12}$, $OC(O)R_{11}$, $OC(O)NR_{11}R_{12}$, $OR_{11}$, $SO_nR_{11}$, $S(O)_nNR_{11}R_{12}$, a heterocyclic ring or bicyclic heterocyclic ring with from 1 to 4 heteroatoms selected from N, O or S which can be optionally substituted by $R_3$, $R_4$ and $R_5$, $C_1$–$C_6$ alkyl or substituted $C_1$–$C_6$ alkyl, unless X is hydrogen or halogen, then $R_8$ is absent; or $R_7$ and $R_8$ taken together form a heterocyclic ring containing one or more heteroatoms selected from N, O or S which can be optionally substituted by $R_3$, $R_4$ and $R_5$; or $R_7$ and $R_8$ taken together form a carbocyclic ring of 3–7 atoms or

when m≠0;

$R_9$ and $R_{9a}$ are independently hydrogen, $C_1$–$C_6$ alkyl, substituted $C_1$–$C_6$ alkyl; aryl or substituted aryl, aralkyl or substituted aralkyl when m≠0; or $R_9$ and $R_{9a}$ taken together for a carbocyclic ring of 3–7 atoms or

when m≠0;

$R_{10}$ and $R_{10a}$ are independently hydrogen, $C_1$–$C_6$ alkyl, substituted $C_1$–$C_6$ alkyl, aryl, substituted aryl, aralkyl or substituted aralkyl; or $R_{10}$ and $R_{10a}$ taken together form a carbocyclic ring of 3–7 atoms or

$R_9$ and $R_{10}$ when taken together form a carbocyclic ring of 3–7 carbon atoms or a heterocyclic ring containing one or more heteroatoms when $m \neq 0$; or $R_9$ and $R_2$ taken together form a heterocyclic ring containing 3–7 carbon atoms and one or more heteroatoms when $m \neq 0$; or $R_{10}$ and $R_2$ taken together form a heterocyclic ring containing 3–7 carbon atoms and one or more heteroatoms;

$R_{11}$ and $R_{12}$ are independently a bond, hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{11}$ and $R_{12}$ when taken together can form an optionally substituted ring of 3–9 atoms;

$R_{13}$ is hydrogen, OH, $NR_7R_8$, $NR_{16}SO_2(C_1$–$C_6$ alkyl), $NR_{16}SO_2$(substituted $C_1$–$C_6$ alkyl), $NR_{16}SO_2$(aryl), $NR_{16}SO_2$(substituted aryl), $NR_{16}SO_2(C_1$–$C_3$ perfluoroalkyl); $SO_2NR_{16}(C_1$–$C_6$ alkyl), $SO_2NR_{11}$ (subsituted $C_1$–$C_6$ alkyl), $SO_2NR_{11}$(aryl), $SO_2NR_{16}$ (substituted aryl), $SO_2NR_{16}(C_1$–$C_3$ perfluoroalkyl); $SO_2NR_{16}(C(O)C_1$–$C_6$ alkyl); $SO_2NR_{16}(C(O)$-substituted $C_1$–$C_6$ alkyl); $SO_2NR_{16}(C(O)$-aryl); $SO_2NR_{16}(C(O)$-substituted aryl); $S(O)_n(C_1$–$C_6$ alkyl); $S(O)_n$(substituted $C_1$–$C_6$ alkyl), $S(O)_n$(aryl), $S(O)_n$ (substituted aryl), $C_1$–$C_3$ perfluoroalkyl, $C_1$–$C_3$ perfluoroalkoxy, $C_1$–$C_6$ alkoxy, substituted $C_1$–$C_6$ alkoxy, COOH, halogen, $NO_2$; or CN;

$R_{14}$ and $R_{15}$ are independently hydrogen, $C_1$–$C_6$ alkyl, substituted $C_1$–$C_6$ alkyl, $C_2$–$C_6$ alkenyl, substituted $C_2$–$C_6$ alkenyl, CN, nitro, $C_1$–$C_3$ perfluoroalkyl, $C_1$–$C_3$ perfluoroalkoxy, aryl, substituted aryl, aralkyl, substituted aralkyl, $R_{16}O(CH_2)_p$—, $R_{16}C(O)O(CH_2)_p$—, $R_{16}OC(O)(CH_2)_p$—, —$(CH_2)_pS(O)_nR_{17}$, —$(CH_2)_pC(O)N(R_{16})_2$ or halogen;

wherein $R_{17}$ is hydrogen, $C_1$–$C_6$ alkyl, $C_1$–$C_3$ perfluoroalkyl, aryl or substituted aryl;

$R_{16}$ is hydrogen, $C_1$–$C_6$ alkyl, substituted $C_1$–$C_6$ alkyl, aryl, substituted aryl, aralkyl, substituted aralkyl, a carbocyclic ring of 3–7 atoms or a substituted carbocyclic ring containing 3–7 atoms;

$R_{18}$ is hydrogen, $C_1$–$C_6$ alkyl, substituted $C_1$–$C_6$ alkyl, $C(O)OR_{16}$, $C(O)N(R_{16})_2$, $C(O)R_{16}$, $S(O)_nR_{16}$;

$R_{19}$ is either the definition of $R_{13}$ or $R_{14}$;

X is N, O, $S(O)_n$, C(O), $(CR_{11}R_{12})_p$, a single bond to $R_8$, $C_2$–$C_6$ alkenyl, substituted $C_2$–$C_6$ alkenyl, $C_2$–$C_6$ alkynyl, or substituted $C_2$–$C_6$ alkynyl; when X is O, $S(O)_n$, C(O), or $CR_{11}R_{12}$ only $R_8$ is possible;

Z is O, S or $NR_{11}$;

m is 0, 1, 2 or 3;

n is 0, 1 or 2;

p is 0, 1, 2, 3 or 4; and the alkyl, cycloalkyl, alkenyl and alkynyl substituents are selected from $C_1$–$C_6$ alkyl, $C_3$–$C_7$ cycloalkyl, aryl, substituted aryl, aralkyl, substituted aralkyl, hydroxy, oxo, cyano, $C_1$–$C_6$ alkoxy, fluoro, $C(O)OR_{11}$, aryl $C_1$–$C_3$ alkoxy, substituted aryl $C_1$–$C_3$ alkoxy, and the aryl substituents are as defined for $R_3$, $R_4$ and $R_5$;

or a pharmaceutically acceptable addition salt and/or hydrate thereof, or where applicable, a geometric or optical isomer or racemic mixture thereof.

2. The compound according to claim 1 of the formula

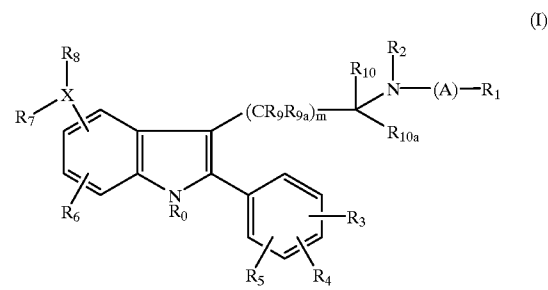

(I)

wherein:

A is $C_1$–$C_6$ alkyl, substituted $C_1$–$C_6$ alkyl or $C_0$–$C_5$ alkyl-$S(O)_n$-$C_0$–$C_5$ alkyl;

$R_0$ is hydrogen;

$R_1$ is

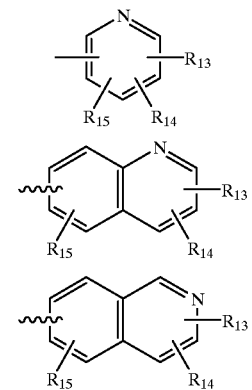

the nitrogen atoms contained in the $R_1$ heteroaromatic rings may exist either as drawn or, when chemically allowed, in their oxidized (N→O) state;

$R_3$, $R_4$ and $R_5$ are independently hydrogen, $C_1$–$C_6$ alkyl, substituted $C_1$–$C_6$ alkyl or halogen;

$R_8$ is $C(O)NR_{11}R_{12}$;

$R_{11}$ and $R_{12}$ are independently a bond, hydrogen, $C_1$–$C_6$ alkyl, substituted $C_1$–$C_6$ alkyl, aryl, substituted aryl, aralkyl, substituted aralkyl, a carbocyclic ring of 3–7 atoms, a substituted carbocyclic ring containing 3–7 atoms, a heterocyclic ring or bicyclic heterocyclic ring with from 1 to 4 heteroatoms selected from N, O or S which can be optionally substituted by $R_3$, $R_4$ and $R_5$, $C_1$–$C_6$-alkyl substituted by a heterocyclic ring or bicyclic heterocyclic ring with from 1 to 4 heteroatoms selected from N, O or S which can be optionally substituted by $R_3$, $R_4$ and $R_5$;

$R_{11}$ and $R_{12}$ when taken together can form an optionally substituted ring of 3–9 atoms;

X is $(CR_{11}R_{12})_p$;

or a pharmaceutically acceptable addition salt and/or hydrate thereof, or where applicable, a geometric or optical isomer or racemic mixture thereof.

3. The compound according to claim 1 of the formula

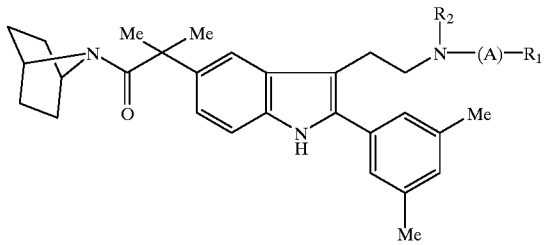

or a pharmaceutically acceptable addition salt and/or hydrate thereof, or where applicable, a geometric or optical isomer or racemic mixture thereof; wherein —(A)—$R_1$ and $R_2$ are as indicated in the table below:

| —(A)—$R_1$ | $R_2$ |
|---|---|
| 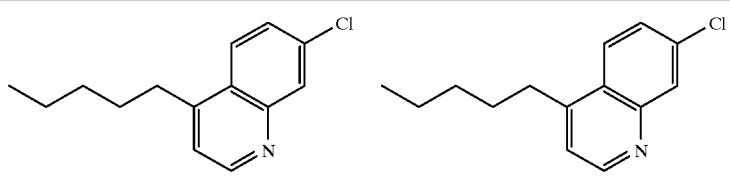 | |

-continued

| —(A)—$R_1$, $R_2$ |
|---|
| 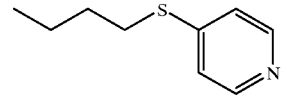 |
| 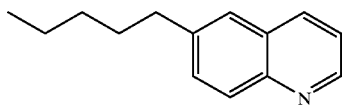 |

4. The compound according to claim 1 of the formula

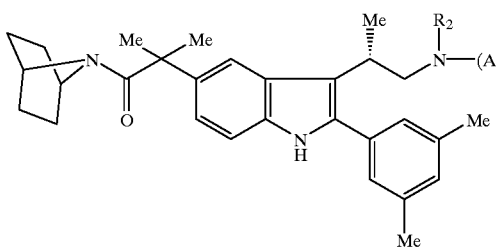

or a pharmaceutically acceptable addition salt and/or hydrate thereof, or where applicable, a geometric or optical isomer or racemic mixture thereof; wherein —(A)—$R_1$ and $R_2$ are as indicated in the table below:

| —(A)—$R_1$, $R_2$ |
|---|
| 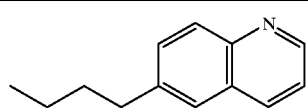 |

5. The compound according to claim 1 of the formula

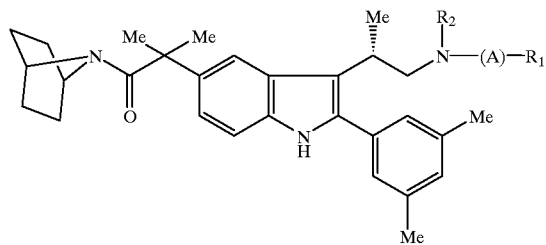

or a pharmaceutically acceptable addition salt and/or hydrate thereof, or where applicable, a geometric or optical isomer or racemic mixture thereof; wherein —(A)—$R_1$ and $R_2$ are as indicated in the table below:

6. The compound according to claim 1 of the formula

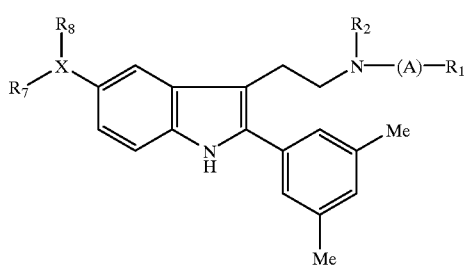

or a pharmaceutically acceptable addition salt and/or hydrate thereof, or where applicable, a geometric or optical isomer or racemic mixture thereof; wherein X—R₇,R₈,—(A)—R₁ and R₂ are as indicated in the table below:

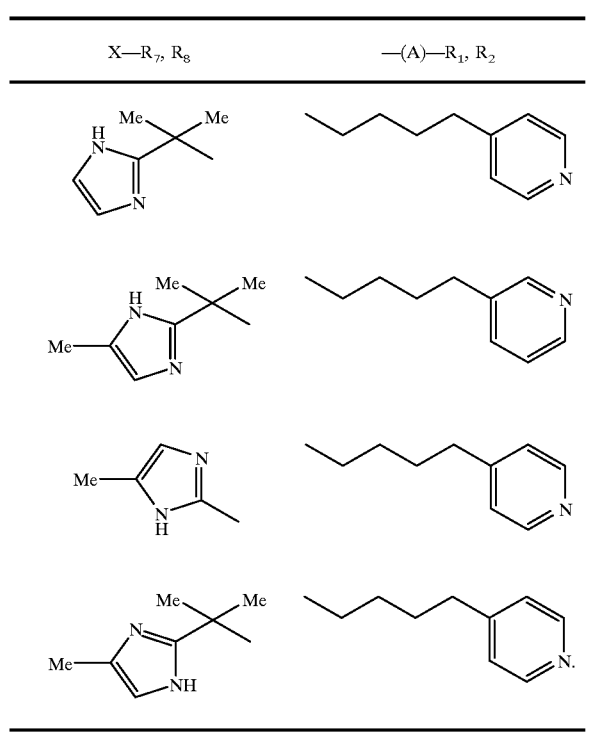

7. The compound according to claim 1 of the formula

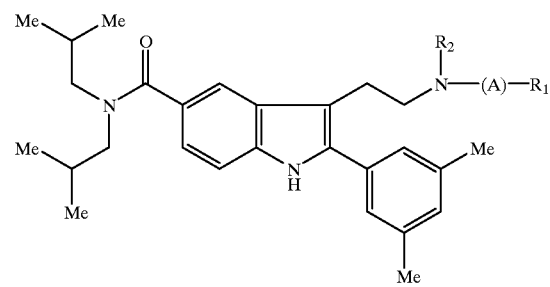

or a pharmaceutically acceptable addition salt and/or hydrate thereof, or where applicable, a geometric or optical isomer or racemic mixture thereof; wherein —(A)—R₁,R₂ is as indicated in the table below:

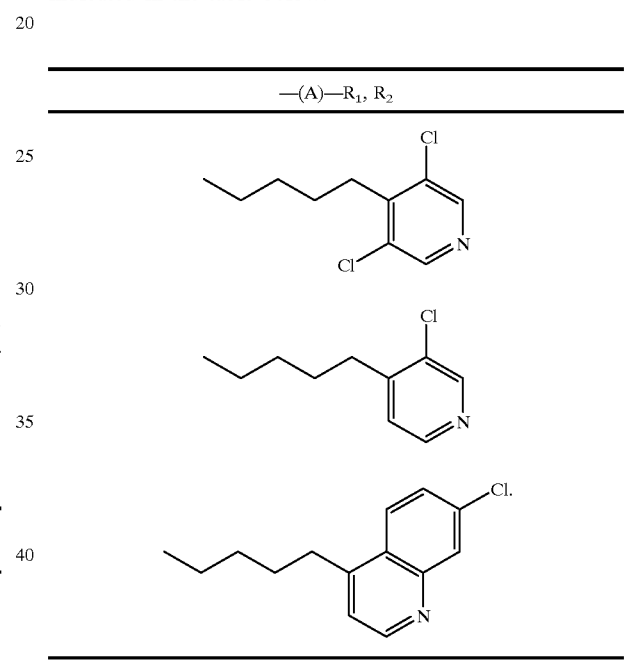

8. A pharmaceutical composition which comprises an effective amount of a compound as defined in claim 1 and a pharmaceutically acceptable carrier therefor.

9. A method for antagonizing gonadotropin-releasing hormone in a subject in need thereof which comprises administering to said subject an effective amount of a compound as defined in claim 1 to a subject suffering from a gonadotropin-releasing hormone derived disorder.

10. A method according to claim 9 wherein the gonadotropin-releasing hormone derived disorder is a sex-hormone related condition.

11. A method according to claim 9 wherein the gonadotropin-releasing hormone derived disorder is a sex hormone dependent cancer, benign prostatic hypertropy or myoma of the uterus.

12. A method according to claim 11 wherein the sex hormone dependent cancer is selected from the group consisting of prostatic cancer, uterine cancer, breast cancer and pituitary gonadotrophe adenomas.

13. A method according to claim 10 wherein the sex hormone related condition is selected from the group consisting of endometriosis, polycystic ovarian disease, uterine fibroids and precocious puberty.

14. A method for preventing pregnancy in a subject in need thereof which comprises administering an effective amount of a compound as defined in claim 1.

15. A method for treating lupus erythematosis in a subject in need thereof which comprises administering to said subject an effective amount of a compound as defined in claim 1.

16. A method for treating irritable bowel syndrome in a subject in need thereof which comprises administering to said subject an effective amount of a compound as defined in claim 1.

17. A method for treating premenstrual syndrome in a subject in need thereof which comprises administering to said subject an effective amount of a compound as defined in claim 1.

18. A method for treating hirsutism in a subject in need thereof which comprises administering to said subject an effective amount of a compound as defined in claim 1.

19. A method for treating a growth hormone deficiency in a subject in need thereof which comprises administering to said subject an effective amount of a compound which stimulates the endogenous production or release of growth hormone and an effective amount of a compound as defined in claim 1.

20. A method for treating sleep disorders in a subject in need thereof which comprises administering to said subject an effective amount of a compound as defined in claim 1.

21. The method according to claim 17 wherein the sleep disorder is sleep apnea.

22. A pharmaceutical composition which comprises an inert carrier and an effective amount of a compound which stimulates the endogenous production or release of growth hormone in combination with a compound as defined in claim 1.

23. A pharmaceutical composition made by combining the compound of claim 1 and a pharmaceutically acceptable carrier therefor.

24. A process for making a pharmaceutical composition comprising combining a compound of claim 1 and a pharmaceutically acceptable carrier.

25. Pharmaceutical therapy comprising co-admirristration of a compound having luteinizing hormone releasing hormone activity with a compound of claim 1.

26. The therapy of claim 25 wherein the compound having luteinizing hormone releasing hormone activity is a peptide compound.

27. The therapy of claim 26 wherein the peptide compound is a natural hormone or an analog thereof.

28. The therapy of claim 26 wherein the peptide compound is a compound selected from the group consisting of leuprorelin, gonadorelin, buserelin, triptorelin, goserelin, nafarelin, histrelin, deslorelin, meterelin and recirelin.

* * * * *